US011845952B2

(12) United States Patent
Okada et al.

(10) Patent No.: US 11,845,952 B2
(45) Date of Patent: Dec. 19, 2023

(54) ADENO-ASSOCIATED VIRUS VECTOR

(71) Applicants: NIPPON MEDICAL SCHOOL FOUNDATION, Tokyo (JP); TEIKA PHARMACEUTICAL CO., LTD., Toyama (JP)

(72) Inventors: Takashi Okada, Tokyo (JP); Tsutomu Igarashi, Tokyo (JP); Asaka Shiozawa, Tokyo (JP)

(73) Assignees: NIPPON MEDICAL SCHOOL FOUNDATION, Tokyo (JP); TEIKA PHARMACEUTICAL CO., LTD., Toyama (JP)

( * ) Notice: Subject to any disclaimer, the term of this patent is extended or adjusted under 35 U.S.C. 154(b) by 327 days.

(21) Appl. No.: 16/968,397

(22) PCT Filed: Jan. 16, 2019

(86) PCT No.: PCT/JP2019/001090
§ 371 (c)(1),
(2) Date: Aug. 7, 2020

(87) PCT Pub. No.: WO2019/155833
PCT Pub. Date: Aug. 15, 2019

(65) Prior Publication Data

US 2020/0399657 A1 Dec. 24, 2020

(30) Foreign Application Priority Data

Feb. 7, 2018 (JP) ................................ 2018-019963

(51) Int. Cl.
*C12N 15/861* (2006.01)
*A61P 27/02* (2006.01)
*A61K 35/761* (2015.01)
*A61K 38/18* (2006.01)
*A61K 39/235* (2006.01)

(52) U.S. Cl.
CPC .......... *C12N 15/861* (2013.01); *A61K 35/761* (2013.01); *A61K 38/1833* (2013.01); *A61K 39/235* (2013.01); *A61P 27/02* (2018.01)

(58) Field of Classification Search
None
See application file for complete search history.

(56) References Cited

U.S. PATENT DOCUMENTS 5,024,939 A 6/1991 Gorman
8,729,041 B2 * 5/2014 Mendell .................. A61P 35/00 435/325
2004/0029106 A1 2/2004 Samulski et al.
2007/0110724 A1 5/2007 Samulski et al.
2009/0149349 A1 6/2009 Robert
2010/0069467 A1 3/2010 Boye et al.
2010/0310516 A1 12/2010 Samulski et al.
2013/0210895 A1 8/2013 Boye et al.
2013/0252325 A1 9/2013 Samulski et al.
2016/0331846 A1 11/2016 Keimel et al.
2017/0304465 A1 * 10/2017 Pechan .............. A61K 48/0058
2018/0298380 A1 10/2018 Gao et al.

FOREIGN PATENT DOCUMENTS

CN 106884014 A 6/2017
JP S63-152986 A 6/1988
JP 2003-512823 A 4/2003
JP 2004-500858 A 1/2004
JP 2013-526854 A 6/2013
WO WO-2003031569 * 4/2003
WO WO-2007/127428 A2 11/2007
WO WO-2016089206 A2 * 6/2016 ........... A61K 38/177
WO WO-2016/172008 A1 10/2016
WO WO-2016/187053 A1 11/2016

(Continued)

OTHER PUBLICATIONS

McCarty et al., Gene Therapy, 2001, 8:1248-1254. (Year: 2001).*
Rodova et al., Plasmid, 2013, 69(3):223-230. (Year: 2013).*
Rosas et al., www.moleculartherapy.org, 2012, 20(11):2098-2110. (Year: 2012).*
Gray et al., Hum Gene Ther., 2011, 22(9):1143-1153. (Year: 2011).*
Database GenSeq Accession No. BDB15422, "Cytomegalovirus (CMV) IE promoter DNA, SEQ ID 10," entered in EBI Database on Jul. 28, 2016 (1 page).

(Continued)

*Primary Examiner* — Nicole Kinsey White
(74) *Attorney, Agent, or Firm* — Clark & Elbing LLP; Susan M. Michaud

(57) ABSTRACT

One disadvantage of adeno-associated virus (AAV) is low gene expression efficiency due to delayed expression of the inserted gene. Provided is a vector plasmid for producing a vector genome to be inserted into an adeno-associated virus (AAV). The vector plasmid is provided with a vector genome cassette as a template of the vector genome, and the vector genome cassette is provided with: (1) an expression cassette including a nucleic acid molecule encoding a target gene and (b) a nucleic acid molecule encoding an expression regulatory region that allows expression of the target gene; and (2) two nucleic acid molecules positioned on both sides of the expression cassette and encoding inverted terminal repeats (ITRs). Also provided is a pharmaceutical composition containing the AVV vector, for treating or preventing an eye disease or disease associated with same. Further provided is a method for treating or preventing the eye disease or disease associated with same, comprising administering a therapeutically effective amount of the pharmaceutical composition for treating or preventing the eye disease or disease associated with same to a subject suffering from the eye disease or disease associated with same.

17 Claims, 5 Drawing Sheets

Specification includes a Sequence Listing.

(56) References Cited

FOREIGN PATENT DOCUMENTS

WO WO-2017/218450 A1 12/2017

OTHER PUBLICATIONS

Extended European Search Report dated Mar. 22, 2021, for European Patent Application No. 19751748.5, Okada et al., "Improved Adeno-Associated Virus Vector," filed Jan. 16, 2019 (11 pages).
Gaddy et al., "In vivo expression of HGF/NK1 and GLP-1 from dsAAV vectors enhances pancreatic β-cell proliferation and improves pathology in the db/db mouse model of diabetes," Diabetes 59(12):3108-3116 (2010).
Igarishi et al., "Tyrosine triple mutated AAV2-BDNF gene therapy in a rat model of transient IOP elevation," Mol. Vis. 22:816-826 (2016).
Natkunarajah et al., "Assessment of ocular transduction using single-stranded and self-complementary recombinant adeno-associated virus serotype 2/8," Gene Ther. 15(6):463-467 (2008).
Ostedgaard et al., "A shortened adeno-associated virus expression cassette for CFTR gene transfer to cystic fibrosis airway epithelia," Proc. Natl. Acad. Sci. U.S.A. 102(8):2952-2957 (2005).
Ryals et al., "Quantifying transduction efficiencies of unmodified and tyrosine capsid mutant AAV vectors in vitro using two ocular cell lines," Mol. Vis. 17:1090-1102 (2011).
International Search Report and Written Opinion, and English Translation of Search Report, for PCT International Application No. PCT/JP2019/001090, dated Apr. 9, 2019 (10 pages).
Rosas et al., "Patterns of scAAV vector insertion associated with oncogenic events in a mouse model for genotoxicity," Mol. Ther. 20(11):2098-2110 (2012).
Suzumura et al., "Adeno-associated virus vector-mediated production of hepatocyte growth factor attenuates liver fibrosis in mice," Hepatol. Int. 2(1):80-88 (2008).
Tomono et al., "Production and purification method for gene transfer virus vectors," Pharma Medica 33:15-22 (2015).

* cited by examiner

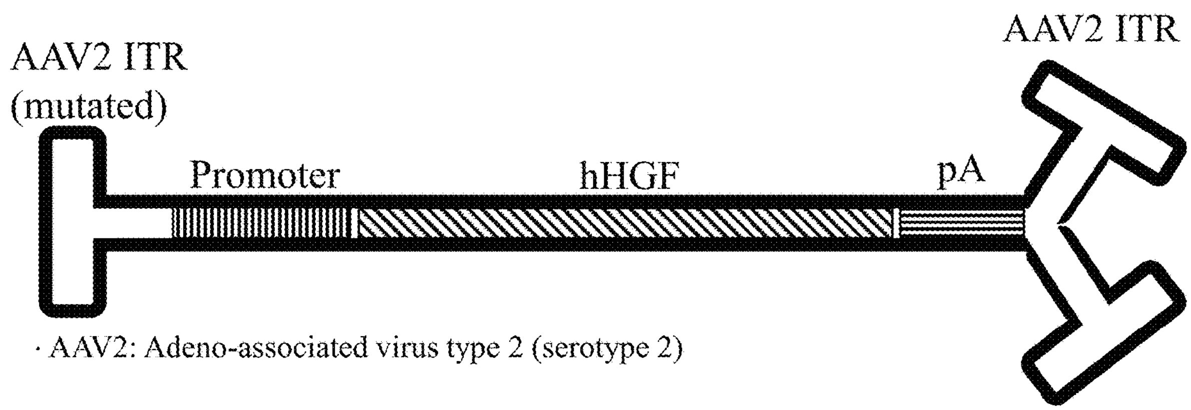

· AAV2: Adeno-associated virus type 2 (serotype 2)

· Promoter: human cytomegalovirus major immediate early (HCMVMIE) promoter region (+ enhancer region)

· hHGF: Human HGF sequence optimized by substituting for human frequent codons

· pA: Simian Virus 40 (SV40) poly A signal

· AAV2 ITR: Inverted terminal repeat (ITR) of AAV

AAV2 ITR(mutated): ITR with a mutated terminal resolution site (TRS)

FIG. 1

CCTGCAGGCAGCTGCGCGCTCGCTCGCTCACTGAGGCCGCCCG
GGCAAAGCCCGGGCGTCGGGCGACCTTTGGTCGCCCGGCCTCA
GTGAGCGAGCGAGCGCGCAGAGAGGGAGTGGGGTTATCGGCGC
GCCGCGGCCGCCCATGGACTAGT-Promoter-TTCTAGAGCT
AGCGAATTCGCTAGCGGCCCAGGCGGCCCACC-Genome-GGC
CAGGCCGGCCGGATCCATTTAAATGATATCGATGATCCAGACA
TGATAAGATACATTGATGAGTTTGGACAAACCACAACTAGAAT
GCAGTGAAAAAAATGCTTTATTTGTGAAATTTGTGATGCTATT
GCTTTATTTGTAACCATTATAAGCTGCAATAAACAAGTTAACA
ACAACAATTGCATTCATTTTATGTTTCAGGTTCAGGGGGAGGT
GTGGGAGGTTTTTTTTAATTAATCTAGAGCGGCCGCAGGAACC
CCTAGTGATGGAGTTGGCCACTCCCTCTCTGCGCGCTCGCTCG
CTCACTGAGGCCGGGCGACCAAAGGTCGCCCGACGCCCGGGCT
TTGCCCGGGCGGCCTCAGTGAGCGAGCGAGCGCGCAGCTGCCT
GCAG

FIG. 2

SEQUENCE LISTING

```
<160> NUMBER OF SEQ ID NOS: 16

<210> SEQ ID NO 1
<211> LENGTH: 930
<212> TYPE: DNA
<213> ORGANISM: Cytomegalovirus

<400> SEQUENCE: 1

aatcaatatt ggccattagc catattattc attggttata tagcataaat caatattggc     60
```

```
tattggccat tgcatacgtt gtatccatat cataatatgt acatttatat tggctcatgt    120

ccaacattac cgccatgttg acattgatta ttgactagtt attaatagta atcaattacg    180

gggtcattag ttcatagccc atatatggag ttccgcgtta cataacttac ggtaaatggc    240

ccgcctggct gaccgcccaa cgacccccgc ccattgacgt caataatgac gtatgttccc    300

atagtaacgc caatagggac tttccattga cgtcaatggg tggagtattt acggtaaact    360

gcccacttgg cagtacatca agtgtatcat atgccaagta cgccccctat tgacgtcaat    420

gacggtaaat ggcccgcctg gcattatgcc cagtacatga ccttatggga ctttcctact    480

tggcagtaca tctacgtatt agtcatcgct attaccatgg tgatgcggtt ttggcagtac    540

atcaatgggc gtggatagcg gtttgactca cggggatttc caagtctcca ccccattgac    600

gtcaatggga gtttgttttg gcaccaaaat caacgggact ttccaaaatg tcgtaacaac    660

tccgccccat tgacgcaaat gggcggtagg cgtgtacggt gggaggtcta tataagcaga    720

gctcgtttag tgaaccgtca gatcgcctgg agacgccatc cacgctgttt tgacctccat    780

agaagacacc gggaccgatc cagcctccgc ggccgggaac ggtgcattgg aacgcggatt    840

ccccgtgcca agagtgacgt aagtaccgcc tatagagtct ataggcccac ccccttggct    900

tcttatgcat gctatactgt ttttggcttg                                     930
```

<210> SEQ ID NO 2
<211> LENGTH: 344
<212> TYPE: DNA
<213> ORGANISM: Artificial Sequence
<220> FEATURE:
<223> OTHER INFORMATION: CMV promoter for p42 (p42CMV)

<400> SEQUENCE: 2

```
attatgccca gtacatgacc ttatgggact ttcctacttg gcagtacatc tacgtattag     60

tcatcgctat taccatggtg atgcggtttt ggcagtacat caatgggcgt ggatagcggt    120

ttgactcacg gggatttcca agtctccacc ccattgacgt caatgggagt ttgttttggc    180

accaaaatca acgggacttt ccaaaatgtc gtaacaactc cgccccattg acgcaaatgg    240

gcggtaggcg tgtacggtgg gaggtctata taagcagagc tcgtttagtg aaccgtcaga    300

tcgcctggag acgccatcca cgctgttttg acctccatag aaga                     344
```

<210> SEQ ID NO 3
<211> LENGTH: 584
<212> TYPE: DNA
<213> ORGANISM: Artificial Sequence
<220> FEATURE:
<223> OTHER INFORMATION: CMV promoter for p13 (p13CMV)

<400> SEQUENCE: 3

```
attaatagta atcaattacg gggtcattag ttcatagccc atatatggag ttccgcgtta     60

cataacttac ggtaaatggc ccgcctggct gaccgcccaa cgacccccgc ccattgacgt    120

caataatgac gtatgttccc atagtaacgc caatagggac tttccattga cgtcaatggg    180

tggagtattt acggtaaact gcccacttgg cagtacatca agtgtatcat atgccaagta    240

cgccccctat tgacgtcaat gacggtaaat ggcccgcctg gcattatgcc cagtacatga    300

ccttatggga ctttcctact tggcagtaca tctacgtatt agtcatcgct attaccatgg    360

tgatgcggtt ttggcagtac atcaatgggc gtggatagcg gtttgactca cggggatttc    420

caagtctcca ccccattgac gtcaatggga gtttgttttg gcaccaaaat caacgggact    480

ttccaaaatg tcgtaacaac tccgccccat tgacgcaaat gggcggtagg cgtgtacggt    540
```

```
gggaggtcta tataagcaga gctcgtttag tgaaccgtca gatc                    584


<210> SEQ ID NO 4
<211> LENGTH: 2187
<212> TYPE: DNA
<213> ORGANISM: Artificial Sequence
<220> FEATURE:
<223> OTHER INFORMATION: Codon optimized human HGF (optHGF) gene
      sequence

<400> SEQUENCE: 4

atgtgggtga ccaagctgct gcccgccctg ctgctgcagc acgtgctgct gcacctgctg     60

ctgctgccca tcgccatccc ctacgccgag ggccagcgga agcggcggaa caccatccac    120

gagttcaaga agagcgccaa gaccaccctg atcaagatcg accccgccct gaagatcaag    180

accaagaagg tgaacaccgc cgaccagtgc gccaaccggt gcacccggaa caagggcctg    240

cccttcacct gcaaggcctt cgtgttcgac aaggcccgga agcagtgcct gtggttcccc    300

ttcaacagca tgagcagcgg cgtgaagaag gagttcggcc acgagttcga cctgtacgag    360

aacaaggact acatccggaa ctgcatcatc ggcaagggcc ggagctacaa gggcaccgtg    420

agcatcacca agagcggcat caagtgccag ccctggagca gcatgatccc ccacgagcac    480

agcttcctgc ccagcagcta ccggggcaag gacctgcagg agaactactg ccggaacccc    540

cggggcgagg agggcggccc ctggtgcttc accagcaacc ccgaggtgcg gtacgaggtg    600

tgcgacatcc cccagtgcag cgaggtggag tgcatgacct gcaacggcga gagctaccgg    660

ggcctgatgg accacaccga gagcggcaag atctgccagc ggtgggacca ccagaccccc    720

caccggcaca agttcctgcc cgagcggtac cccgacaagg gcttcgacga caactactgc    780

cggaaccccg acggccagcc ccggccctgg tgctacaccc tggaccccca cacccggtgg    840

gagtactgcg ccatcaagac ctgcgccgac aacaccatga acgacaccga cgtgcccctg    900

gagaccaccg agtgcatcca gggccagggc gagggctacc ggggcaccgt gaacaccatc    960

tggaacggca tcccctgcca gcggtgggac agccagtacc cccacgagca cgacatgacc   1020

cccgagaact tcaagtgcaa ggacctgcgg gagaactact gccggaaccc cgacggcagc   1080

gagagcccct ggtgcttcac caccgacccc aacatccggg tgggctactg cagccagatc   1140

cccaactgcg acatgagcca cggccaggac tgctaccggg gcaacggcaa gaactacatg   1200

ggcaacctga gccagacccg gagcggcctg acctgcagca tgtgggacaa gaacatggag   1260

gacctgcacc ggcacatctt ctgggagccc gacgccagca agctgaacga gaactactgc   1320

cggaaccccg acgacgacgc ccacggcccc tggtgctaca ccggcaaccc cctgatcccc   1380

tgggactact gccccatcag ccggtgcgag ggcgacacca cccccaccat cgtgaacctg   1440

gaccaccccg tgatcagctg cgccaagacc aagcagctgc gggtggtgaa cggcatcccc   1500

acccggacca acatcggctg gatggtgagc ctgcggtacc ggaacaagca catctgcggc   1560

ggcagcctga tcaaggagag ctgggtgctg accgcccggc agtgcttccc cagccgggac   1620

ctgaaggact acgaggcctg gctgggcatc cacgacgtgc acggccgggg cgacgagaag   1680

tgcaagcagg tgctgaacgt gagccagctg gtgtacggcc ccgagggcag cgacctggtg   1740

ctgatgaagc tggcccggcc cgccgtgctg gacgacttcg tgagcaccat cgacctgccc   1800

aactacggct gcaccatccc cgagaagacc agctgcagcg tgtacggctg gggctacacc   1860

ggcctgatca actacgacgg cctgctgcgg gtggcccacc tgtacatcat gggcaacgag   1920

aagtgcagcc agcaccaccg gggcaaggtg accctgaacg agagcgagat ctgcgccggc   1980
```

```
gccgagaaga tcggcagcgg cccctgcgag ggcgactacg gcggcccccct ggtgtgcgag   2040

cagcacaaga tgcggatggt gctgggcgtg atcgtgcccg gccggggctg cgccatcccc   2100

aaccggcccg gcatcttcgt gcgggtggcc tactacgcca agtggatcca caagatcatc   2160

ctgacctaca aggtgcccca gagctga                                        2187
```

<210> SEQ ID NO 5
<211> LENGTH: 4955
<212> TYPE: DNA
<213> ORGANISM: Artificial Sequence
<220> FEATURE:
<223> OTHER INFORMATION: pVector-p42

<400> SEQUENCE: 5

```
ccaatgatcc tgcaggcagc tgcgcgctcg ctcgctcact gaggccgccc gggcaaagcc     60

cgggcgtcgg gcgacctttg gtcgcccggc ctcagtgagc gagcgagcgc gcagagaggg    120

agtggggtta tcggcgcgcc gcggccgccc atggactagt attatgccca gtacatgacc    180

ttatgggact ttcctacttg gcagtacatc tacgtattag tcatcgctat taccatggtg    240

atgcggtttt ggcagtacat caatgggcgt ggatagcggt ttgactcacg gggatttcca    300

agtctccacc ccattgacgt caatgggagt ttgttttggc accaaaatca acgggacttt    360

ccaaaatgtc gtaacaactc cgccccattg acgcaaatgg gcggtaggcg tgtacggtgg    420

gaggtctata taagcagagc tcgtttagtg aaccgtcaga tcgcctggag acgccatcca    480

cgctgttttg acctccatag aagattctag agctagcgaa ttcgctagcg gcccaggcgg    540

cccaccatgt gggtgaccaa gctgctgccc gccctgctgc tgcagcacgt gctgctgcac    600

ctgctgctgc tgcccatcgc catcccctac gccgagggcc agcggaagcg gcggaacacc    660

atccacgagt tcaagaagag cgccaagacc accctgatca agatcgaccc cgccctgaag    720

atcaagacca agaaggtgaa caccgccgac cagtgcgcca accggtgcac ccggaacaag    780

ggcctgccct tcacctgcaa ggccttcgtg ttcgacaagg cccggaagca gtgcctgtgg    840

ttccccttca acagcatgag cagcggcgtg aagaaggagt tcggccacga gttcgacctg    900

tacgagaaca aggactacat ccggaactgc atcatcggca agggccggag ctacaagggc    960

accgtgagca tcaccaagag cggcatcaag tgccagccct ggagcagcat gatcccccac   1020

gagcacagct tcctgcccag cagctaccgg ggcaaggacc tgcaggagaa ctactgccgg   1080

aacccccggg gcgaggaggg cggcccctgg tgcttcacca gcaaccccga ggtgcggtac   1140

gaggtgtgcg acatccccca gtgcagcgag gtggagtgca tgacctgcaa cggcgagagc   1200

taccggggcc tgatggacca caccgagagc ggcaagatct gccagcggtg ggaccaccag   1260

accccccacc ggcacaagtt cctgcccgag cggtaccccg acaagggctt cgacgacaac   1320

tactgccgga accccgacgg ccagccccgg ccctggtgct acaccctgga cccccacacc   1380

cggtgggagt actgcgccat caagacctgc gccgacaaca ccatgaacga caccgacgtg   1440

cccctggaga ccaccgagtg catccagggc cagggcgagg gctaccgggg caccgtgaac   1500

accatctgga acggcatccc ctgccagcgg tgggacagcc agtacccccca cgagcacgac   1560

atgacccccg agaacttcaa gtgcaaggac ctgcgggaga actactgccg gaaccccgac   1620

ggcagcgaga gcccctggtg cttcaccacc gaccccaaca tccgggtggg ctactgcagc   1680

cagatcccca actgcgacat gagccacggc caggactgct accggggcaa cggcaagaac   1740

tacatgggca acctgagcca gacccggagc ggcctgacct gcagcatgtg ggacaagaac   1800
```

-continued

```
atggaggacc tgcaccggca catcttctgg gagcccgacg ccagcaagct gaacgagaac   1860
tactgccgga accccgacga cgacgcccac ggcccctggt gctacaccgg caaccccctg   1920
atcccctggg actactgccc catcagccgg tgcgagggcg acaccacccc caccatcgtg   1980
aacctggacc accccgtgat cagctgcgcc aagaccaagc agctgcgggt ggtgaacggc   2040
atccccaccc ggaccaacat cggctggatg gtgagcctgc ggtaccggaa caagcacatc   2100
tgcggcggca gcctgatcaa ggagagctgg gtgctgaccg cccggcagtg cttccccagc   2160
cgggacctga aggactacga ggcctggctg ggcatccacg acgtgcacgg ccggggcgac   2220
gagaagtgca agcaggtgct gaacgtgagc cagctggtgt acggccccga gggcagcgac   2280
ctggtgctga tgaagctggc ccggcccgcc gtgctggacg acttcgtgag caccatcgac   2340
ctgcccaact acggctgcac catccccgag aagaccagct gcagcgtgta cggctggggc   2400
tacaccggcc tgatcaacta cgacggcctg ctgcgggtgg cccacctgta catcatgggc   2460
aacgagaagt gcagccagca ccaccggggc aaggtgaccc tgaacgagag cgagatctgc   2520
gccggcgccg agaagatcgg cagcggcccc tgcgagggcg actacggcgg cccccctggtg   2580
tgcgagcagc acaagatgcg gatggtgctg ggcgtgatcg tgcccggccg gggctgcgcc   2640
atccccaacc ggcccggcat cttcgtgcgg gtggcctact acgccaagtg gatccacaag   2700
atcatcctga cctacaaggt gccccagagc tgaggccagg ccggccggat ccatttaaat   2760
gatatcgatg atccagacat gataagatac attgatgagt ttggacaaac cacaactaga   2820
atgcagtgaa aaaaatgctt tatttgtgaa atttgtgatg ctattgcttt atttgtaacc   2880
attataagct gcaataaaca agttaacaac aacaattgca ttcattttat gtttcaggtt   2940
cagggggagg tgtgggaggt tttttttaat taatctagag cggccgcagg aacccctagt   3000
gatggagttg gccactccct ctctgcgcgc tcgctcgctc actgaggccg ggcgaccaaa   3060
ggtcgcccga cgcccgggct ttgcccgggc ggcctcagtg agcgagcgag cgcgcagctg   3120
cctgcaggat cggaaagaac atgtgagcaa aaggccagca aaaggccagg aaccgtaaaa   3180
aggccgcgtt gctggcgttt ttccataggc tccgcccccc tgacgagcat cacaaaaatc   3240
gacgctcaag tcagaggtgg cgaaacccga caggactata aagataccag gcgtttcccc   3300
ctggaagctc cctcgtgcgc tctcctgttc cgaccctgcc gcttaccgga tacctgtccg   3360
cctttctccc ttcgggaagc gtggcgcttt ctcatagctc acgctgtagg tatctcagtt   3420
cggtgtaggt cgttcgctcc aagctgggct gtgtgcacga accccccgtt cagcccgacc   3480
gctgcgcctt atccggtaac tatcgtcttg agtccaaccc ggtaagacac gacttatcgc   3540
cactggcagc agccactggt aacaggatta gcagagcgag gtatgtaggc ggtgctacag   3600
agttcttgaa gtggtggcct aactacggct acactagaag aacagtattt ggtatctgcg   3660
ctctgctgaa gccagttacc ttcggaaaaa gagttggtag ctcttgatcc ggcaaacaaa   3720
ccaccgctgg tagcggtggt ttttttgttt gcaagcagca gattacgcgc agaaaaaaag   3780
gatctcaaga agatcctttg atcttttcta cggggtctga cgctcagtgg aacgaaaact   3840
cacgttaagg gattttggtc atgagattat caaaaaggat cttcacctag atccttttaa   3900
attaaaaatg aagttttaaa tcaatctaaa gtatatatga gtaaacttgg tctgacagtt   3960
accaatgctt aatcagtgag gcacctatct cagcgatctg tctatttcgt tcatccatag   4020
ttgcctgact ccccgtcgtg tagataacta cgatacggga gggcttacca tctggcccca   4080
gtgctgcaat gataccgcga gacccacgct caccggctcc agatttatca gcaataaacc   4140
agccagccgg aagggccgag cgcagaagtg gtcctgcaac tttatccgcc tccatccagt   4200
```

```
ctattaattg ttgccgggaa gctagagtaa gtagttcgcc agttaatagt ttgcgcaacg   4260

ttgttgccat tgctacaggc atcgtggtgt cacgctcgtc gtttggtatg gcttcattca   4320

gctccggttc ccaacgatca aggcgagtta catgatcccc catgttgtgc aaaaaagcgg   4380

ttagctcctt cggtcctccg atcgttgtca gaagtaagtt ggccgcagtg ttatcactca   4440

tggttatggc agcactgcat aattctctta ctgtcatgcc atccgtaaga tgcttttctg   4500

tgactggtga gtactcaacc aagtcattct gagaatagtg tatgcggcga ccgagttgct   4560

cttgcccggc gtcaatacgg gataataccg cgccacatag cagaacttta aaagtgctca   4620

tcattggaaa acgttcttcg gggcgaaaac tctcaaggat cttaccgctg ttgagatcca   4680

gttcgatgta acccactcgt gcacccaact gatcttcagc atcttttact ttcaccagcg   4740

tttctgggtg agcaaaaaca ggaaggcaaa atgccgcaaa aaagggaata agggcgacac   4800

ggaaatgttg aatactcata ctcttccttt ttcaatatta ttgaagcatt tatcagggtt   4860

attgtctcat gagcggatac atatttgaat gtatttagaa aaataaacaa ataggggttc   4920

cgcgcacatt tccccgaaaa gtgccacctg acgtc                              4955
```

```
<210> SEQ ID NO 6
<211> LENGTH: 5788
<212> TYPE: DNA
<213> ORGANISM: Artificial Sequence
<220> FEATURE:
<223> OTHER INFORMATION: pVector-p13

<400> SEQUENCE: 6

ccaatgatcc tgcaggcagc tgcgcgctcg ctcgctcact gaggccgccc gggcaaagcc     60

cgggcgtcgg gcgacctttg gtcgcccggc ctcagtgagc gagcgagcgc gcagagaggg    120

agtggccaac tccatcacta ggggttcctg cggccgccca tggactagta ttaatagtaa    180

tcaattacgg ggtcattagt tcatagccca tatatggagt tccgcgttac ataacttacg    240

gtaaatggcc cgcctggctg accgcccaac gacccccgcc cattgacgtc aataatgacg    300

tatgttccca tagtaacgcc aatagggact ttccattgac gtcaatgggt ggagtattta    360

cggtaaactg cccacttggc agtacatcaa gtgtatcata tgccaagtac gccccctatt    420

gacgtcaatg acggtaaatg gcccgcctgg cattatgccc agtacatgac cttatgggac    480

tttcctactt ggcagtacat ctacgtatta gtcatcgcta ttaccatggt gatgcggttt    540

tggcagtaca tcaatgggcg tggatagcgg tttgactcac ggggatttcc aagtctccac    600

cccattgacg tcaatgggag tttgttttgg caccaaaatc aacgggactt tccaaaatgt    660

cgtaacaact ccgccccatt gacgcaaatg ggcggtaggc gtgtacggtg ggaggtctat    720

ataagcagag ctcgtttagt gaaccgtcag atcgaattcg ctagcggccc aggcggccca    780

ccatgtgggt gaccaagctg ctgcccgccc tgctgctgca gcacgtgctg ctgcacctgc    840

tgctgctgcc catcgccatc ccctacgccg agggccagcg gaagcggcgg aacaccatcc    900

acgagttcaa gaagagcgcc aagaccaccc tgatcaagat cgacccccgcc ctgaagatca    960

agaccaagaa ggtgaacacc gccgaccagt gcgccaaccg gtgcacccgg aacaagggcc   1020

tgcccttcac ctgcaaggcc ttcgtgttcg acaaggcccg gaagcagtgc ctgtggttcc   1080

ccttcaacag catgagcagc ggcgtgaaga aggagttcgg ccacgagttc gacctgtacg   1140

agaacaagga ctacatccgg aactgcatca tcggcaaggg ccggagctac aagggcaccg   1200

tgagcatcac caagagcggc atcaagtgcc agccctggag cagcatgatc ccccacgagc   1260
```

-continued

```
acagcttcct gcccagcagc taccggggca aggacctgca ggagaactac tgccggaacc   1320
cccggggcga ggagggcggc ccctggtgct tcaccagcaa ccccgaggtg cggtacgagg   1380
tgtgcgacat cccccagtgc agcgaggtgg agtgcatgac ctgcaacggc gagagctacc   1440
ggggcctgat ggaccacacc gagagcggca agatctgcca gcggtgggac caccagaccc   1500
cccaccggca caagttcctg cccgagcggt accccgacaa gggcttcgac gacaactact   1560
gccggaaccc cgacggccag ccccggccct ggtgctacac cctggacccc cacacccggt   1620
gggagtactg cgccatcaag acctgcgccg acaacaccat gaacgacacc gacgtgcccc   1680
tggagaccac cgagtgcatc cagggccagg gcgagggcta ccggggcacc gtgaacacca   1740
tctggaacgg catcccctgc cagcggtggg acagccagta cccccacgag cacgacatga   1800
cccccgagaa cttcaagtgc aaggacctgc gggagaacta ctgccggaac cccgacggca   1860
gcgagagccc ctggtgcttc accaccgacc ccaacatccg ggtgggctac tgcagccaga   1920
tccccaactg cgacatgagc cacggccagg actgctaccg gggcaacggc aagaactaca   1980
tgggcaacct gagccagacc cggagcggcc tgacctgcag catgtgggac aagaacatgg   2040
aggacctgca ccggcacatc ttctgggagc ccgacgccag caagctgaac gagaactact   2100
gccggaaccc cgacgacgac gcccacggcc cctggtgcta caccggcaac cccctgatcc   2160
cctgggacta ctgccccatc agccggtgcg agggcgacac cacccccacc atcgtgaacc   2220
tggaccaccc cgtgatcagc tgcgccaaga ccaagcagct gcgggtggtg aacggcatcc   2280
ccacccggac caacatcggc tggatggtga gcctgcggta ccggaacaag cacatctgcg   2340
gcggcagcct gatcaaggag agctgggtgc tgaccgcccg gcagtgcttc cccagccggg   2400
acctgaagga ctacgaggcc tggctgggca tccacgacgt gcacggccgg ggcgacgaga   2460
agtgcaagca ggtgctgaac gtgagccagc tggtgtacgg ccccgagggc agcgacctgg   2520
tgctgatgaa gctggcccgg cccgccgtgc tggacgactt cgtgagcacc atcgacctgc   2580
ccaactacgg ctgcaccatc cccgagaaga ccagctgcag cgtgtacggc tggggctaca   2640
ccggcctgat caactacgac ggcctgctgc gggtggccca cctgtacatc atgggcaacg   2700
agaagtgcag ccagcaccac cggggcaagg tgaccctgaa cgagagcgag atctgcgccg   2760
gcgccgagaa gatcggcagc ggcccctgcg agggcgacta cggcggcccc ctggtgtgcg   2820
agcagcacaa gatgcggatg gtgctgggcg tgatcgtgcc cggccggggc tgcgccatcc   2880
ccaaccggcc cggcatcttc gtgcgggtgg cctactacgc caagtggatc cacaagatca   2940
tcctgaccta caaggtgccc cagagctgag gccaggccgg ccggatccat cgataatcaa   3000
cctctggatt acaaaatttg tgaaagattg actgatattc ttaactatgt tgctcctttt   3060
acgctgtgtg gatatgctgc tttaatgcct ctgtatcatg ctattgcttc ccgtacggct   3120
ttcgttttct cctccttgta taaatcctgg ttgctgtctc tttatgagga gttgtggccc   3180
gttgtccgtc aacgtggcgt ggtgtgctct gtgtttgctg acgcaacccc cactggctgg   3240
ggcattgcca ccacctgtca actcctttct gggactttcg ctttccccct cccgatcgcc   3300
acggcagaac tcatcgccgc ctgccttgcc cgctgctgga caggggctag gttgctgggc   3360
actgataatt ccgtggtgtt gtcggggaaa tcatcgtcct ttccttggct gctcgcctgt   3420
gttgccaact ggatcctgcg cgggacgtcc ttctgctacg tcccttcggc tctcaatcca   3480
gcggacctcc cttcccgagg ccttctgccg gttctgcggc ctctcccgcg tcttcgcttt   3540
cggcctccga cgagtcggat ctccctttgg gccgcctccc cgcctattta aatgatatcg   3600
atgatccaga catgataaga tacattgatg agtttggaca aaccacaact agaatgcagt   3660
```

```
gaaaaaaatg ctttatttgt gaaatttgtg atgctattgc tttatttgta accattataa   3720
gctgcaataa acaagttaac aacaacaatt gcattcattt tatgtttcag gttcaggggg   3780
aggtgtggga ggttttttt aattaatcta gagcggccgc aggaacccct agtgatggag   3840
ttggccactc cctctctgcg cgctcgctcg ctcactgagg ccgggcgacc aaaggtcgcc   3900
cgacgcccgg gctttgcccg ggcggcctca gtgagcgagc gagcgcgcag ctgcctgcag   3960
gatcggaaag aacatgtgag caaaaggcca gcaaaaggcc aggaaccgta aaaaggccgc   4020
gttgctggcg tttttccata ggctccgccc ccctgacgag catcacaaaa atcgacgctc   4080
aagtcagagg tggcgaaacc cgacaggact ataaagatac caggcgtttc cccctggaag   4140
ctccctcgtg cgctctcctg ttccgaccct gccgcttacc ggatacctgt ccgcctttct   4200
cccttcggga agcgtggcgc tttctcatag ctcacgctgt aggtatctca gttcggtgta   4260
ggtcgttcgc tccaagctgg gctgtgtgca cgaacccccc gttcagcccg accgctgcgc   4320
cttatccggt aactatcgtc ttgagtccaa cccggtaaga cacgacttat cgccactggc   4380
agcagccact ggtaacagga ttagcagagc gaggtatgta ggcggtgcta cagagttctt   4440
gaagtggtgg cctaactacg gctacactag aagaacagta tttggtatct gcgctctgct   4500
gaagccagtt accttcggaa aaagagttgg tagctcttga tccggcaaac aaaccaccgc   4560
tggtagcggt ggtttttttg tttgcaagca gcagattacg cgcagaaaaa aaggatctca   4620
agaagatcct ttgatctttt ctacggggtc tgacgctcag tggaacgaaa actcacgtta   4680
agggattttg gtcatgagat tatcaaaaag gatcttcacc tagatccttt taaattaaaa   4740
atgaagtttt aaatcaatct aaagtatata tgagtaaact tggtctgaca gttaccaatg   4800
cttaatcagt gaggcaccta tctcagcgat ctgtctattt cgttcatcca tagttgcctg   4860
actccccgtc gtgtagataa ctacgatacg ggagggctta ccatctggcc ccagtgctgc   4920
aatgataccg cgagacccac gctcaccggc tccagattta tcagcaataa accagccagc   4980
cggaagggcc gagcgcagaa gtggtcctgc aactttatcc gcctccatcc agtctattaa   5040
ttgttgccgg gaagctagag taagtagttc gccagttaat agtttgcgca acgttgttgc   5100
cattgctaca ggcatcgtgg tgtcacgctc gtcgtttggt atggcttcat tcagctccgg   5160
ttcccaacga tcaaggcgag ttacatgatc ccccatgttg tgcaaaaaag cggttagctc   5220
cttcggtcct ccgatcgttg tcagaagtaa gttggccgca gtgttatcac tcatggttat   5280
ggcagcactg cataattctc ttactgtcat gccatccgta agatgctttt ctgtgactgg   5340
tgagtactca accaagtcat tctgagaata gtgtatgcgg cgaccgagtt gctcttgccc   5400
ggcgtcaata cgggataata ccgcgccaca tagcagaact ttaaaagtgc tcatcattgg   5460
aaaacgttct tcggggcgaa aactctcaag gatcttaccg ctgttgagat ccagttcgat   5520
gtaacccact cgtgcaccca actgatcttc agcatctttt actttcacca gcgtttctgg   5580
gtgagcaaaa acaggaaggc aaaatgccgc aaaaaaggga ataagggcga cacggaaatg   5640
ttgaatactc atactcttcc tttttcaata ttattgaagc atttatcagg gttattgtct   5700
catgagcgga tacatatttg aatgtattta gaaaaataaa caaatagggg ttccgcgcac   5760
atttccccga aaagtgccac ctgacgtc                                      5788
```

<210> SEQ ID NO 7
<211> LENGTH: 592
<212> TYPE: DNA
<213> ORGANISM: Artificial Sequence
<220> FEATURE:

<223> OTHER INFORMATION: Woodchuck Hepatitis Virus Post-transcriptional
      Regulatory Element(WPRE)-mut6 sequence

<400> SEQUENCE: 7

```
taatcaacct ctggattaca aaatttgtga aagattgact gatattctta actatgttgc      60

tccttttacg ctgtgtggat atgctgcttt aatgcctctg tatcatgcta ttgcttcccg     120

tacggctttc gttttctcct ccttgtataa atcctggttg ctgtctcttt atgaggagtt     180

gtggcccgtt gtccgtcaac gtggcgtggt gtgctctgtg tttgctgacg caacccccac     240

tggctggggc attgccacca cctgtcaact cctttctggg actttcgctt tccccctccc     300

gatcgccacg gcagaactca tcgccgcctg ccttgcccgc tgctggacag gggctaggtt     360

gctgggcact gataattccg tggtgttgtc ggggaaatca tcgtcctttc cttggctgct     420

cgcctgtgtt gccaactgga tcctgcgcgg gacgtccttc tgctacgtcc cttcggctct     480

caatccagcg gacctccctt cccgaggcct tctgccggtt ctgcggcctc tcccgcgtct     540

tcgctttcgg cctccgacga gtcggatctc cctttgggcc gcctccccgc ct             592
```

<210> SEQ ID NO 8
<211> LENGTH: 20
<212> TYPE: DNA
<213> ORGANISM: Artificial Sequence
<220> FEATURE:
<223> OTHER INFORMATION: Forward primer for optHGF

<400> SEQUENCE: 8

```
taccggaaca agcacatctg                                                  20
```

<210> SEQ ID NO 9
<211> LENGTH: 18
<212> TYPE: DNA
<213> ORGANISM: Artificial Sequence
<220> FEATURE:
<223> OTHER INFORMATION: Reverse primer for optHGF

<400> SEQUENCE: 9

```
ttcatcagca ccaggtcg                                                    18
```

<210> SEQ ID NO 10
<211> LENGTH: 20
<212> TYPE: DNA
<213> ORGANISM: Artificial Sequence
<220> FEATURE:
<223> OTHER INFORMATION: Forward primer for GAPDH

<400> SEQUENCE: 10

```
catcactgcc acccagaaga                                                  20
```

<210> SEQ ID NO 11
<211> LENGTH: 15
<212> TYPE: DNA
<213> ORGANISM: Artificial Sequence
<220> FEATURE:
<223> OTHER INFORMATION: Reverse primer for GAPDH

<400> SEQUENCE: 11

```
atgttctggg cagcc                                                       15
```

<210> SEQ ID NO 12
<211> LENGTH: 121
<212> TYPE: DNA
<213> ORGANISM: Artificial Sequence
<220> FEATURE:

<223> OTHER INFORMATION: Mutant-type ITR sequence

<400> SEQUENCE: 12
ctgcgcgctc gctcgctcac tgaggccgcc cgggcaaagc ccgggcgtcg ggcgaccttt 60
ggtcgcccgg cctcagtgag cgagcgagcg cgcagagagg gagtggggtt atcggcgcgc 120
c 121

<210> SEQ ID NO 13
<211> LENGTH: 130
<212> TYPE: DNA
<213> ORGANISM: Artificial Sequence
<220> FEATURE:
<223> OTHER INFORMATION: Non mutant-type 3'-ITR sequence

<400> SEQUENCE: 13
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag 130

<210> SEQ ID NO 14
<211> LENGTH: 130
<212> TYPE: DNA
<213> ORGANISM: Artificial Sequence
<220> FEATURE:
<223> OTHER INFORMATION: Non mutant-type 5'-ITR sequence

<400> SEQUENCE: 14
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct 130

<210> SEQ ID NO 15
<211> LENGTH: 196
<212> TYPE: DNA
<213> ORGANISM: Simian virus

<400> SEQUENCE: 15
gatccagaca tgataagata cattgatgag tttggacaaa ccacaactag aatgcagtga 60
aaaaaatgct ttatttgtga aatttgtgat gctattgctt tatttgtaac cattataagc 120
tgcaataaac aagttaacaa caacaattgc attcatttta tgtttcaggt tcagggggag 180
gtgtgggagg ttttt 196

<210> SEQ ID NO 16
<211> LENGTH: 2424
<212> TYPE: DNA
<213> ORGANISM: Artificial Sequence
<220> FEATURE:
<223> OTHER INFORMATION: pVector (empty vector)

<400> SEQUENCE: 16
ccaatgatcc tgcaggcagc tgcgcgctcg ctcgctcact gaggccgccc gggcaaagcc 60
cgggcgtcgg gcgacctttg gtcgcccggc ctcagtgagc gagcgagcgc gcagagaggg 120
agtggggtta tcggcgcgcc gcggccgccc atggactagt ttctagagct agcgaattcg 180
ctagcggccc aggcggccca ccggccaggc cggccggatc catttaaatg atatcgatga 240
tccagacatg ataagataca ttgatgagtt tggacaaacc acaactagaa tgcagtgaaa 300
aaaatgcttt atttgtgaaa tttgtgatgc tattgcttta tttgtaacca ttataagctg 360

```
caataaacaa gttaacaaca acaattgcat tcattttatg tttcaggttc agggggaggt    420
gtgggaggtt tttttaatt aatctagagc ggccgcagga acccctagtg atggagttgg    480
ccactccctc tctgcgcgct cgctcgctca ctgaggccgg gcgaccaaag gtcgcccgac    540
gcccgggctt tgcccgggcg gcctcagtga gcgagcgagc gcgcagctgc ctgcaggatc    600
ggaaagaaca tgtgagcaaa aggccagcaa aaggccagga accgtaaaaa ggccgcgttg    660
ctggcgtttt tccataggct ccgcccccct gacgagcatc acaaaaatcg acgctcaagt    720
cagaggtggc gaaacccgac aggactataa agataccagg cgtttccccc tggaagctcc    780
ctcgtgcgct ctcctgttcc gaccctgccg cttaccggat acctgtccgc ctttctccct    840
tcgggaagcg tggcgctttc tcatagctca cgctgtaggt atctcagttc ggtgtaggtc    900
gttcgctcca agctgggctg tgtgcacgaa ccccccgttc agcccgaccg ctgcgcctta    960
tccggtaact atcgtcttga gtccaacccg gtaagacacg acttatcgcc actggcagca   1020
gccactggta acaggattag cagagcgagg tatgtaggcg gtgctacaga gttcttgaag   1080
tggtggccta actacggcta cactagaaga acagtatttg gtatctgcgc tctgctgaag   1140
ccagttacct tcggaaaaag agttggtagc tcttgatccg gcaaacaaac caccgctggt   1200
agcggtggtt tttttgtttg caagcagcag attacgcgca gaaaaaaagg atctcaagaa   1260
gatcctttga tcttttctac ggggtctgac gctcagtgga acgaaaactc acgttaaggg   1320
attttggtca tgagattatc aaaaaggatc ttcacctaga tccttttaaa ttaaaaatga   1380
agttttaaat caatctaaag tatatatgag taaacttggt ctgacagtta ccaatgctta   1440
atcagtgagg cacctatctc agcgatctgt ctatttcgtt catccatagt tgcctgactc   1500
cccgtcgtgt agataactac gatacgggag ggcttaccat ctggccccag tgctgcaatg   1560
ataccgcgag acccacgctc accggctcca gatttatcag caataaacca gccagccgga   1620
agggccgagc gcagaagtgg tcctgcaact ttatccgcct ccatccagtc tattaattgt   1680
tgccgggaag ctagagtaag tagttcgcca gttaatagtt tgcgcaacgt tgttgccatt   1740
gctacaggca tcgtggtgtc acgctcgtcg tttggtatgg cttcattcag ctccggttcc   1800
caacgatcaa ggcgagttac atgatccccc atgttgtgca aaaaagcggt tagctccttc   1860
ggtcctccga tcgttgtcag aagtaagttg gccgcagtgt tatcactcat ggttatggca   1920
gcactgcata attctcttac tgtcatgcca tccgtaagat gcttttctgt gactggtgag   1980
tactcaacca agtcattctg agaatagtgt atgcggcgac cgagttgctc ttgcccggcg   2040
tcaatacggg ataataccgc gccacatagc agaactttaa aagtgctcat cattggaaaa   2100
cgttcttcgg ggcgaaaact ctcaaggatc ttaccgctgt tgagatccag ttcgatgtaa   2160
cccactcgtg cacccaactg atcttcagca tcttttactt tcaccagcgt ttctgggtga   2220
gcaaaaacag gaaggcaaaa tgccgcaaaa aagggaataa gggcgacacg gaaatgttga   2280
atactcatac tcttcctttt tcaatattat tgaagcattt atcagggtta ttgtctcatg   2340
agcggataca tatttgaatg tatttagaaa aataaacaaa taggggttcc gcgcacattt   2400
ccccgaaaag tgccacctga cgtc                                           2424
```

ADENO-ASSOCIATED VIRUS VECTOR

SEQUENCE LISTING

The instant application contains a Sequence Listing which has been submitted electronically in ASCII format and is hereby incorporated by reference in its entirety. Said ASCII copy, created on Aug. 6, 2020, is named 51007-019001_Sequence_Listing_08.07.20_ST25 and is 26,963 bytes in size.

TECHNICAL FIELD

The present invention is related to an improved adeno-associated virus vector.

Typical examples of causes of blindness in Japan are glaucoma and retinitis pigmentosa. With regard to glaucoma, some patients have advanced stages even though their intraocular pressure are well controlled. As for retinitis pigmentosa, there is still no effective treatment due to various causative genes. Therefore, there are needs for a treatment to protect retinal tissue itself, particularly retinal ganglion cells, photoreceptor cells and retinal pigment epithelium cells themselves.

Discovered as a cell growth factor involved in hepatocyte regeneration, hepatocyte growth factor (HGF) has recently been reported to have a neuroprotective effect and has been studied as a therapeutic agent for central nervous system diseases such as amyotrophic lateral sclerosis and Parkinson's disease. However, there are major problems in using HGF as therapeutic agents for eye diseases. For example, eye drops have a problem that HGF does not reach the target tissues. In addition, since HGF protein have a short half-life in intraocular injections, a high dose and frequent administration are required. This imposes a large burden on patients which makes intraocular injections unrealistic. Therefore, instead of administering HGF protein itself, it is desired to realize HGF production in the target tissues and maintain a long-term pharmacological action of HGF by administering viruses carrying HGF gene.

Regarding the viruses carrying the HGF gene, for example, Non-Patent Document 1 discloses that HGF is expressed in mouse liver using adeno-associated virus type 5 (AAV5).

PRIOR ART DOCUMENT

Non-Patent Document

Non-Patent Document 1: Suzumura K, et al., Adeno-associated virus vector-mediated production of hepatocyte growth factor attenuates liver fibrosis in mice, Hepatol Int (2008) 2: 80-88.

SUMMARY OF THE INVENTION

Problems to be Solved by the Invention

However, the adeno-associated virus (AAV) used in the Non-Patent Document 1 has a problem. That is, due to delayed expression of a carried gene, gene expression efficiency is low. The cause of this is that single-strand adeno-associated virus (ssAAV) are used as AAV. Common AAV is ssAAV and since a ssAAV genome is a single-stranded DNA, the ssAAV genome needs to form a double-stranded DNA in a nucleus of a target cell in order to express a gene carried in the ssAAV. It is considered that the low gene expression efficiency due to the delayed expression occurs in the process in which the ssAAV changes from the single-stranded DNA to the double-stranded DNA.

The purpose of this invention is to solve the problem above.

Means for Solving the Problem

The present invention provides a vector plasmid for producing a vector genome to be carried in an adeno-associated virus (AAV) vector, including a vector genome cassette as a template of the vector genome, in which the vector plasmid includes:

(1) an expression cassette containing (a) a target gene-encoding nucleic acid molecule, and (b) an expression control region-encoding nucleic acid molecule capable of controlling expression of the target gene; and (2) two inverted terminal repeat (ITR)-encoding nucleic acid molecules located so as to sandwich the expression cassette.

According to this vector plasmid, it is possible to replicate a vector genome to be carried in an adeno-associated virus (AAV) vector capable of expressing proteins encoded by a target gene.

It can also provide an AAV vector carrying a vector genome replicated from the above vector plasmid. This makes it possible to provide an AAV vector capable of expressing proteins encoded by a target gene.

In addition, a pharmaceutical composition for treating or preventing an eye disease or a disease associated therewith can be provided. The pharmaceutical composition includes the AAV vector. This makes it possible to provide the AAV vector as a pharmaceutical composition.

In addition, a method for treating or preventing an eye disease or a disease associated therewith can be provided. The method includes administering to a subject suffering from the eye disease or the disease associated therewith a therapeutically effective amount of the pharmaceutical composition for treating or preventing the eye disease or the disease associated therewith. By administering the AAV vector to the subject, the eye disease of the subject or the disease associated therewith can be treated or prevented.

BRIEF DESCRIPTION OF DRAWINGS

FIG. 1 shows a schematic structure of a vector genome according to the present invention.

FIG. 2 shows insertion positions of promoter (corresponding to "Promoter") and HGF (corresponding to "Genome") in PVector-p42 (SEQ ID NO: 5).

DESCRIPTION OF EMBODIMENTS

Figure 3:
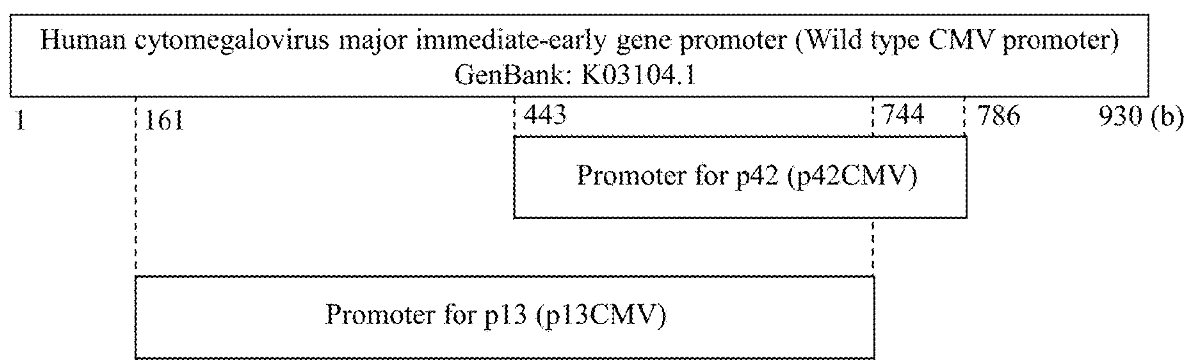
FIG. 3 shows positions of truncated cytomegalovirus promoters for p42 and p13 in a human cytomegalovirus promoter.

Hereinafter, embodiments of the present invention are illustrated in detail. The following embodiments are illustrative only and do not limit the scope of the present invention. In order to avoid redundancy, explanation for similar contents is not repeated.

Definition

For convenience, certain terms employed in the context of the present disclosure are collected here. Unless defined otherwise, all technical and scientific terms used herein have the same meaning as commonly understood by one of the ordinary skilled in the art to which this invention belongs. The singular forms "a", "an", and "the" are used herein to include plural referents unless the context clearly dictates otherwise.

The term "subject" and "patient" are used interchangeably herein and are intended to mean an animal including the human species that is treatable by the vector and pharmaceutical composition of the present invention. The term "subject" or "patient" intended to refer to both the male and female gender unless one gender is specifically indicated. Accordingly, the term "subject" or "patient" comprises any mammal which may benefit from the vector and pharmaceutical composition of the present disclosure. Examples of a "subject" or "patient" can include, but are not limited to, a human, rat, mouse, guinea pig, monkey, pig, goat, cow, horse, dog, cat, bird and fowl. In an exemplary embodiment, "subject" or "patient" is a human.

Notwithstanding that the numerical ranges and parameters setting forth the broad scope of the invention are approximations, the numerical values set forth in the specific examples are described as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

Unless otherwise specified, the nucleotide sequences in the present specification, drawings and sequence listing are described in order from 5' end to 3' end. For example, "100th base" means the 100th base from 5' end. The term "reverse complementary sequence" means a sequence that is in a reverse complementary relationship to a sequence. For example, a reverse complementary sequence of 5'-AAATTCGG-3' is 5'-CCGAATTT-3'.

The nucleotide sequence of the nucleic acid molecule according to the present embodiment (for example, region, cassette, genome and vector plasmid) is:

(i) a nucleotide sequence having 95% or more sequence homology with the nucleotide sequence of the nucleic acid molecule according to the present embodiment;

(ii) a nucleotide sequence in which one or several nucleotides are deleted, substituted, or added in the nucleotide sequence of the nucleic acid molecule according to the present embodiment; or (iii) a nucleotide sequence capable of hybridizing, under stringent conditions, with a complementary sequence of the nucleotide sequence of the nucleic acid molecule according to the present embodiment.

Identity score and homology score in this specification can be calculated by using the known programs such as BLAST. A nucleotide sequence having sequence homology with the nucleic acid molecule according to the present embodiment may have at least 95% sequence homology, such as 96% or more, 97% or more, 98% or more, 99% or more, 99.5% or more, 99.8% or more sequence homology.

In the present specification, the term "several nucleotides" in the expression "nucleotide sequence in which one or several nucleotides are deleted, substituted, or added" is, for example, 2 to 10 bases, 2 to 9 bases, 2 to 8 bases, 2 to 7 bases, 2 to 6 bases, 2 to 5 bases, 2 to 4 bases, 2 to 3 bases or 2 bases preferably. It is generally preferable that the number of bases for the deletion, the substitution or the addition is as small as possible. Any combination of base deletion, substitution and addition may exist at the same time. The base deletion, substitution and addition can be generated by using known techniques.

In the present specification, the term "stringent conditions" includes, for example, the following (1), (2) and the like:

(1) low ionic strength and high washing temperature (e.g., 0.015 M NaCl, 0.0015 M sodium citrate and 0.1% SDS at 50° C.); and (2) use of denaturants such as formamide during a hybridization (e.g., 0.1% bovine serum albumin, 0.1% Ficoll, 0.1% polyinyl pyrrolidone, 50 mM sodium phosphate buffer (pH 6.5), 750 mM NaCl and 75 mM sodium citrate in 50% formamide (vol/vol) at 42° C.). Another example includes 50% formamide, 5×SSC (0.75 M NaCl, 0.075 M sodium citrate), 50 mM sodium phosphate (pH 6.8), 0.1% sodium pyrophosphate, 5×Denhardt's solution, Sonicated Salmon sperm DNA (50 μg/ml), 0.1% SDS, 10% dextran sulfate, temperature 42° C., washing temperature 42° C., 0.2×SSC and 0.1% SDS.

Those skilled in the art will appreciate that the stringent conditions can be suitably modified to obtain clear and detectable hybridization signals.

DETAILED DESCRIPTION OF EMBODIMENTS

In this embodiment, it is provided that a vector plasmid for producing a vector genome to be carried in an adeno-associated virus (AAV) vector, including a vector genome cassette as a template of the vector genome, in which the vector plasmid includes:

(1) an expression cassette including (a) a target gene-encoding nucleic acid molecule, and (b) an expression control region-encoding nucleic acid molecule capable of controlling expression of the target gene; and (2) two inverted terminal repeat (ITR)-encoding nucleic acid molecules located so as to sandwich the expression cassette.

Vector Plasmid

The vector plasmid in this embodiment produces a vector genome to be carried in an adeno-associated virus (AAV) vector in host cells. As the host cell, any host cell (for example, HEK293 cell) can be used as long as the vector genome can be produced from the vector plasmid. The vector plasmid in this embodiment may be provided with an arbitrary selection marker (for example, a nucleic acid molecule encoding an ampicillin resistance gene). The vector plasmid in this embodiment may not have a nucleic acid molecule encoding a gene involved in insertion into a chromosome of the host cell. In an embodiment, the vector plasmid does not have at least one of a nucleic acid molecule encoding a rep gene and a nucleic acid molecule encoding a cap gene. In an embodiment, the vector plasmid has any nucleic acid molecule (e.g., a nucleic acid molecule encoding simian virus 40 (SV40) poly A signal).

In an embodiment, the vector genome is produced from the vector genome cassette as a template. The vector genome may be single-stranded or double-stranded due to self-complementary binding. The vector genome includes a product produced from the vector genome cassette (primary product) and a product produced by using the primary product as a template (secondary product). However, it is sufficient that the target vector genomes are dominant among these products (primary and secondary products). For example, 80, 85, 90, 95 or 99% or more of these products are the target vector genomes.

The vector genome cassette according to the present embodiment includes the expression cassette and two ITR-encoding nucleic acid molecules located so as to sandwich the expression cassette.

In an embodiment, the vector genome cassette may have any number of nucleotides between the ITR located at 5' side and the expression cassette. For example, the number of nucleotides between the ITR and the expression cassette may be within a range from about 3 to about 20 (for example, 3, 4, 5, 6, 7, 8, 9, 10, 11, 12, 13, 14, 15, 16, 17, 18, 19 and 20), and may be between any two values within the range (for example, 3 to 8 and 12 to 16).

In an embodiment, the vector genome cassette may have any number of nucleotides between the expression cassette and the ITR located at 3' side. For example, the number of nucleotides between the expression cassette and the ITR located at 3' side may be within a range from about 200 to about 270 (for example, 200, 205, 210, 215, 220, 225, 230, 235, 240, 245, 250, 255, 260, 265 and 270), and may be between any two values within the range (for example, 200 to 260). In an embodiment, a nucleic acid molecule encoding a poly A signal (for example, a SV40 poly A signal (SEQ ID NO: 15)) is included between the expression cassette and the ITR located at 3' side.

The expression cassette is also included in the vector genome. The expression cassette refers to a nucleic acid molecule encoding a group of genes that are expressed in cells infected with AAV vectors containing the vector genome for treatment or prevention. The expression cassette according to the present embodiment includes (a) the target gene-encoding nucleic acid molecule, and (b) the expression control region-encoding nucleic acid molecule capable of controlling expression of the target gene.

In an embodiment, the vector genome cassette may have any number of nucleotides between the target gene region and the expression control region. For example, the number of nucleotides between the target gene region and the expression control region may be within a range from about 30 to about 70 (for example, 30, 35, 40, 45, 50, 55, 60, 65 and 70), and may be between any two values within the range (for example, 35 to 45).

In an embodiment, the target gene may be any gene. In an embodiment, the target gene is an HGF gene. In an embodiment, the expression control region is a truncated expression control region.

HGF Gene

The vector plasmid in this embodiment includes an HGF gene-encoding nucleic acid molecule. The HGF gene in the present embodiment may be derived from the same species as subjects or patients to be treated or may be derived from a different species therefrom. In an embodiment, the HGF gene is a human HGF gene. The HGF gene may have a nucleotide sequence replaced with a frequent codon in a subject or patient species to be treated. In an embodiment, the human HGF gene has a nucleotide sequence replaced with a human frequent codon. In an embodiment, the human HGF gene has a nucleotide sequence of SEQ ID NO: 4.

Truncated Expression Control Region

The vector plasmid in this embodiment includes the truncated expression control region-encoding nucleic acid molecule capable of controlling expression of the HGF gene. A length of the truncated expression control region in this embodiment is shorter than a length of a native expression control region thereof. Although the truncated expression control region is shorter than the native expression control region thereof, it retains an ability for controlling the expression of the HGF gene. Therefore, the truncated expression control region may lack one or more nucleotide sequences of any length in the native expression control region thereof, as long as it retains the ability controlling the expression of the HGF gene. The truncated expression control region in this embodiment has a function as a promoter. In an embodiment, the truncated expression control region has a functional promoter region and an enhancer region. In an embodiment, the length of the truncated expression control region is between any two values selected from the group consisting of 70%, 65%, 60%, 55%, 50%, 45%, 40%, 35% and 30% of the native expression control region thereof. In another embodiment, the truncated expression control region has an improved ability for controlling the expression of the HGF gene in comparison with the native expression control region thereof.

In one embodiment, the native expression control region includes a cytomegalovirus expression control region. In another, the cytomegalovirus expression control region is a human cytomegalovirus expression control region. In another, the native expression control region is an original (non-genetically engineered) expression control region in an organism or a known artificial expression control region. In another, the term “native” can be put into wild type. In another, the human cytomegalovirus expression control region includes a human cytomegalovirus major immediate early (HCMVMIE) promoter region. In another, the human cytomegalovirus expression control region includes the HCMVMIE promoter region and an enhancer region. In the other, the human cytomegalovirus expression control region includes or consists of a nucleotide sequence of SEQ ID NO: 1 (GenBank: K03104.1).

When the native expression control region includes or consists of the nucleotide sequence of SEQ ID NO: 1, the truncated expression control region has:

(a) a nucleotide sequence between any one of the following 5' end bases; 150, 155, 156, 157, 158, 159, 160, 161, 162, 163, 164, 165, 166, 167, 168, 169, 170, 175, 180, 190, 200, 250, 300, 350, 400, 410, 420, 430, 435, 436, 437, 438, 439, 440, 441, 442, 443, 444, 445, 446, 447, 448, 449, 450, 460 or 470th base, and any one of the following 3' end bases; 700, 710, 720, 730, 735, 736, 737, 738, 739, 740, 741, 742, 743, 744, 745, 746, 747, 748, 749, 750, 751, 752, 753, 754, 755, 760, 765, 770, 750, 760, 770, 775, 776, 777, 778, 779, 780, 781, 782, 783, 784, 785, 786, 787, 788, 789, 790, 791, 792, 793, 794, 795, 796, 797, 798, 799 or 800th base;

(b) a nucleotide sequence between any one of the following 5' end bases; 156, 157, 158, 159, 160, 161, 162, 163, 164, 165 or 166th base, and any one of the following 3' end bases; 739, 740, 741, 742, 743, 744, 745, 746, 747, 748 or 749th base;

(c) a nucleotide sequence between any one of the following 5' end bases; 438, 439, 440, 441, 442, 443, 444, 445, 446, 447 or 448th base, and any one of the following 3' terminal bases; 781, 782, 783, 784, 785, 786, 787, 788, 789, 790 or 791th base;

(d) a nucleotide sequence of SEQ ID NO: 2; or (e) a nucleotide sequence of SEQ ID NO: 3.

Inverted Terminal Repeat (ITR)

The vector plasmid in the present embodiment includes two ITR-encoding nucleic acid molecules located so as to sandwich the expression cassette. The two ITR-encoding nucleic acid molecules in the present embodiment refer to the configuration sandwiching the expression cassette. Therefore, the vector plasmid according to the present embodiment may have an additional ITR-encoding nucleic acid molecule outside a segment (that is, the vector genome cassette) between ITRs as long as it exerts its function (including production of the vector genome to be carried in AAV vector). The ITR functions as an origin of replication for the vector genome cassette and is also involved in packaging into viral particles. In an embodiment, the two ITR-encoding nucleic acid molecules are a non-mutated ITR-encoding nucleic acid molecule and a mutated ITR-encoding nucleic acid molecule. In an embodiment, the mutated ITR-encoding nucleic acid molecule is located upstream (5' end direction) from the non-mutated ITR-encoding nucleic acid molecule in the vector plasmid. In one embodiment, the mutated ITR-encoding nucleic acid molecule has a mutation configured such that the vector genome capable of self-complementation is obtained from the vector genome cassette. In another embodiment, the vector genome includes the expression cassette, a reverse complementary expression cassette including a nucleic acid molecule encoding a reverse complementary sequence of the expression cassette, and the mutated ITR-encoding nucleic acid molecule located between the expression cassette and the reverse complementary expression cassette. Therefore, in such vector genome, the expression cassette and the reverse complementary cassette can bind to each other in a self-complementary manner (for example, see FIG. 1). The ITR-encoding nucleic acid molecule in the vector genome of the present embodiment can form a stem-loop structure. In the other embodiment, the vector genome includes the mutated ITR-encoding nucleic acid molecule, the non-mutated ITR-encoding nucleic acid molecule, and a nucleic acid molecule encoding a reverse complementary sequence of the non-mutated ITR.

In an embodiment, a length of the non-mutated ITR-encoding nucleic acid molecule and a length of the mutant ITR-encoding nucleic acid molecule are shorter than a length of a native ITR encoding nucleic acid molecule thereof. In an embodiment, the ITR-encoding nucleic acid molecule includes a terminal resolution site (TRS)-encoding nucleic acid molecule, and the mutated ITR-encoding nucleic acid molecule has the above mutation in the TRS-encoding nucleic acid molecule. In the embodiment, the mutated ITR-encoding nucleic acid molecule has the above mutation and is shorter than a wild type ITR-encoding nucleic acid molecule. In another embodiment, the two ITR-encoding nucleic acid molecules are both non-mutated ITR-encoding nucleic acid molecules. The two non-mutated ITR-encoding nucleic acid molecules may have the same sequence as or different sequences from each other. In an embodiment, the mutated ITR-encoding nucleic acid molecule includes or consists of a nucleotide sequence of SEQ ID NO: 12. In an embodiment, the non-mutated ITR-encoding nucleic acid molecule includes or consists of a nucleotide sequence of SEQ ID NO: 13 or SEQ ID NO: 14. In an embodiment, one non-mutated ITR-encoding nucleic acid molecule includes or consists of the nucleotide sequence of SEQ ID NO: 13, and the other non-mutated ITR-encoding nucleic acid molecule includes or consists of the nucleotide sequence of SEQ ID NO: 14. In an embodiment, the nucleic acid molecule encoding the non-mutated ITR located at the 5' end side includes or consists of the nucleotide sequence of SEQ ID NO: 14, and the nucleic acid molecule encoding the non-mutated ITR located at the 3' end side includes or consists of the nucleotide sequence of SEQ ID NO: 13. In an embodiment, the nucleotide sequence of the non-mutated ITR located at the 5' end side is in a reverse complementary relationship with the nucleotide sequence of the non-mutated ITR located at the 3' end side. Therefore, the nucleotide sequence of SEQ ID NO: 13 is in a reverse complementary relationship with the nucleotide sequence of SEQ ID NO: 14.

In this embodiment, the mutated ITR-encoding nucleic acid molecule including or consisting of the nucleotide sequence of SEQ ID NO: 12 is provided.

In the present embodiment, the AAV vector carrying the vector genome produced from the above vector plasmid is provided. In an embodiment, the AAV vector is capable of protecting retinal tissue itself, particularly retinal ganglion cells, photoreceptor cells and retinal pigment epithelial cells themselves. As a result of such protection, abnormalities in retinal tissue (particularly retinal ganglion cells, photoreceptor cells and retinal pigment epithelial cells) can be suppressed, and diseases or symptoms caused by such abnormalities can be treated. In an embodiment, the AAV vector is composed of a capsid protein and a genomic vector contained therein. A serotype of the AAV vector is not particularly limited as long as it can be used for treating or preventing an eye disease or a disease associated therewith. In an embodiment, the AAV vector is an AAV serotype 2 (AAV2) vector. In an embodiment, the serotype of the AAV vector is the tyrosine variant AAV2 (Y444, 500, 730F). The AAV vector in the present embodiment may carry a single-strand (ss) type vector genome or may carry a self-complementary (sc) type vector genome.

Eye Diseases or Diseases Associated Therewith

In this embodiment, the AAV vector for treating or preventing the eye disease or the disease associated therewith is provided. In an embodiment, the eye diseases also include ocular symptoms and findings. In an embodiment, the treatment also includes reduction of the disease (symptoms or findings thereof). Although the eye disease may be associated with a disease (symptom or finding) other than the eye disease, the AAV vector of the present embodiment relates to at least treatment or prevention for the eye disease or the disease associated therewith. For example, for subarachnoid hemorrhage, the AAV vector of the present embodiment refers to at least treatment or prevention for an eye disease (for example, retinopathy (e.g., proliferative vitreoretinopathy)) caused by subarachnoid hemorrhage. In at least one embodiment, the eye disease or the disease associated therewith is selected from the group consisting of eyelid disease, lacrimal disease, conjunctival disease, corneal disease, scleral disease, glaucoma, retinitis pigmentosa, retinitis pigmentosa sine pigmento, lens disease, orbital disease, uveal disease, retinal disease, vitreous disease. In an embodiment, retinitis pigmentosa is with or without syndromes of other organs. Examples of retinitis pigmentosa with syndromes of other organs include Usher syndrome, Laurence-Moon syndrome, Bardet-Biedl syndrome, Cockayne syndrome, Batten syndrome, Hunter syndrome, Hurler syndrome, spinocerebellar degeneration and Kearns-Sayre syndrome. In an embodiment, retinitis pigmentosa includes typical retinitis pigmentosa and atypical retinitis pigmentosa. Glaucoma includes primary glaucoma, open-angle glaucoma, angle-closure glaucoma, congenital glaucoma and secondary glaucoma.

In another embodiment, eye disease or the disease associated therewith is selected from the group consisting of soft drusen, reticular pseudodrusen, typical age-related macular degeneration, polypoidal choroidal vasculopathy, retinal angiomatous proliferation, dry age-related macular degeneration, angioid streaks, idiopathic choroidal neovascularization, central serous chorioretinopathy, chronic central serous chorioretinopathy, bullous retinal detachment (multifocal posterior pigment epitheliopathy), posterior vitreous detachment, preretinal membrane, macular hole, vitreomacular traction syndrome, lamellar macular hole, optic disc pit-maculopathy, macular telangiectasia type 1, macular telangiectasia type 2, hypotony maculopathy, branch retinal vein occlusion, central retinal vein occlusion, branch retinal artery occlusion, central retinal artery occlusion, simple diabetic retinopathy, pre-proliferative diabetic retinopathy, proliferative diabetic retinopathy, diabetic macular edema, retinal arterial microaneurysm, Coats disease, Eales disease, Takayasu disease, radiation retinopathy, ocular ischemic syndrome, triangular syndrome, retinitis pigmentosa, retinitis pigmentosa sine pigmento, Leber congenital amaurosis, pigmented paravenous retinochoroidal atrophy, cone-rod dystrophy, fundus albipunctatus, retinitis punctata albescens, Oguchi disease, congenital stationary night blindness, rod monochromatism (achromatopsia), blue cone monochromacy, blue cone amplification syndrome, vitelliform macular dystrophy (Best disease), adult vitelliform macular dystrophy, autosomal recessive bestrophinopathy, Stargardt disease, occult macular dystrophy (Miyake's disease), central areolar choroidal dystrophy, congenital retinoschisis, familial exudative vitreoretinopathy, Stickler syndrome, choroideremia, Bietti crystalline retinopathy, gyrate atrophy of choroid and retina, myelinated nerve fiber of retina, hypertrophy of retinal pigment epithelium, congenital retinal fold, rubella retinopathy, nevus of Ota, neurofibromatosis type 1 (von Recklinghausen disease), tuberous sclerosis complex (Bourneville-Pringle disease), von Hippel-Lindau disease, Sturge-Weber syndrome, Wyburn-Mason syndrome, albinism, retinopathy of prematurity, incontinentia pigmenti, shaken baby syndrome, acute zonal occult outer retinopathy, multiple evanescent white dot syndrome, punctate inner choroidopathy, multifocal choroiditis, acute posterior multifocal placoid pigment epitheliopathy, acute retinal pigment epithelitis, acute idiopathic maculopathy, acute macular neuroretinopathy, geographic choroiditis, Behcet's disease, sarcoidosis, Harada disease, scleritis, optic disc anomaly, optic neuritis, ischemic optic neuropathy, Leber's hereditary optic neuropathy, papilledema, optic disc swelling, optic atrophy, glaucomatous optic neuropathy, retrograde optic atrophy associated with visual pathway pathology, toxic optic neuropathy, traumatic optic neuropathy, systemic lupus erythematosus, antineutrophil cytoplasmic antibody-associated vasculitis, anemic retinopathy, leukemic retinopathy, hyperviscosity syndrome, lipemia retinalis, lysosomal storage disease, Kearns-Sayre syndrome, cancer-associated retinopathy, melanoma associated retinopathy, bilateral diffuse uveal melanocytic proliferation (BDUMP), subarachnoid hemorrhage (Terson syndrome), hypertension, arteriosclerosis, renal retinopathy, pregnancy-induced hypertension, chorioretinal disorder due to blunt trauma, solar retinopathy, retinal disorder due to laser (including industrial laser) photocoagulation, laser pointer retinopathy, hydroxychloroquine retinopathy, interferon-associated retinopathy, tamoxifen retinopathy and paclitaxel retinopathy.

Pharmaceutical Composition

In this embodiment, a pharmaceutical composition for treating or preventing the eye disease or the disease associated therewith, including the AAV vector, is provided. In an embodiment, the pharmaceutical composition includes a therapeutically effective amount of the AAV vector. The pharmaceutical composition of this embodiment may be other types such as suspensions, viscous, semi-viscous gels, solids and semi-solid compositions. The pharmaceutical composition of the present embodiment may include other components such as a pharmaceutically acceptable isotonicity agent, buffer solution, preservative, surfactant and viscosity imparting agent.

The isotonic agents are known to the person skilled in the ophthalmic arts, which include, but are not limited to, glycerin, mannitol, sorbitol, sodium chloride, and other electrolytes.

The pharmaceutical composition of this embodiment may include an effective amount of buffer to maintain its pH at about 6 to about 8, preferably about 7. The buffers are known to the person skilled in the ophthalmic arts, which include, but are not limited to, acetate, ascorbate, borate, bicarbonate, carbonate, citrate, L-Histidine buffer and phosphate buffer.

The preservatives are known to the person skilled in the ophthalmic arts, which include, but are not limited to, benzalkonium chloride, thimerosal, chlorobutanol, methylparaben, propylparaben, phenylethyl alcohol, disodium edetate, sorbic acid, polyquaternium-1, stabilized oxychloro complex (also known as Purite®)), phenylmercuric acetate, chlorobutanol, benzyl alcohol and other agents known to the person skilled in the art.

The surfactants are known to the person skilled in the ophthalmic arts, which may be, but are not limited to, polyethoxylated castor oil, polysorbates 20, 60 and 80, Pluronic® F-68, F-84 and P-103 (BASF Corp., Parsippany NJ, USA), cyclodextrins, polysorbates, poloxamers, alcohol ethoxylates, ethylene glycol-propylene glycol block copolymers, fatty acid amides, alkylphenol ethoxylates, phospholipids or other agents known to the person skilled in the art.

The therapeutically effective amount of the AAV vector may be within a range from about $1\times10^{8}$ to about $1\times10^{20}$ vector genomes (for example, $1\times10^{5}$ vector genomes, $1\times10^{6}$ vector genomes, $1\times10^{7}$ vector genomes, $1\times10^{8}$ vector genomes, $1\times10^{9}$ vector genomes, $1\times10^{10}$ vector genomes, $1\times10^{11}$ vector genomes, $1\times10^{12}$ vector genomes, $1\times10^{13}$ vector genomes, $1\times10^{14}$ vector genomes, $1\times10^{15}$ vector genomes, $1\times10^{16}$ vector genomes, $1\times10^{17}$ vector genomes, $1\times10^{18}$ vector genomes, $1\times10^{19}$ vector genomes and $1\times10^{26}$ vector genomes), and may be between any two values within the range. The amount of the AAV vector may be a single dose or multiple doses. The pharmaceutical composition of the present embodiment may be administered by eye drops, subretinal administration, subinternal limiting membrane administration, or intravitreal administration.

The pharmaceutical composition is administered in an effective amount to treat or prevent the eye disease or the disease associated therewith whether the pharmaceutical composition is administered alone or in combination with other therapeutic agents. However, the total dose of the AAV vector of the present embodiment is determined by attending physicians within the scope of appropriate medical judgment. The effective amount for the subject will depend on the severity, age, body weight, general health, sex and diet of the subject; time of administration; route of administration; rate of excretion or degradation of the AAV vector of the present embodiment; duration of treatment; and drugs used in combination with or concurrently with the pharmaceutical composition. The dose of the pharmaceutical composition may not be constant in each administration. For example, it may be administered at a dose lower than a dose required to achieve a desired effect, and then the dose may be gradually increased until the desired effect is obtained.

Method for Treating or Preventing the Eye Diseases or the Diseases Associated Therewith In this embodiment, a method for treating or preventing the eye disease or the disease associated therewith, including administering to a subject suffering from the eye disease or the disease associated therewith a therapeutically effective amount of the pharmaceutical composition for treating or preventing the eye disease or the disease associated therewith, including the AAV vector is provided.

In this specification, as techniques of molecular biology (e.g., techniques such as cloning, plasmid extraction, DNA fragment cleavage, ligation, hybridization, site-specific mutagenesis, PCR and Western blotting), well-known ordinary methods can be used. These methods can be found in Sambrook, J., Fritsch, E. F., and Maniatis, T., "Molecular Cloning A Laboratory Manual, Second Edition", Cold Spring Harbor Laboratory Press, (1989).

EXAMPLES

Hereinafter, the present invention will be further described with reference to examples, but the present invention is not limited thereto.

Example 1

Construction of Recombinant Adeno-Associated Virus (rAAV) Vector

An rAAV vector was constructed using an adenovirus free system. FIG. 1 shows a schematic structure of a self-complementary rAAV vector genome carrying hHGF.

scAAV2TM.mCMV.optHGF

As the rAAV vector, a self-complementary scAAV2TM.p42CMV.optHGF (other names: p42 or AAV.p42) was prepared. First, a vector plasmid of SEQ ID NO: 5 (pVector-p42) was constructed according to a method commonly used by the person skilled in the art. FIG. 2 shows insertion positions of a promoter (corresponding to Promoter) and HGF (corresponding to Genome) in pVector-p42. A truncated cytomegalovirus promoter is composed of a nucleotide sequence from 443th base to 786th base in the wild-type human cytomegalovirus major immediate early (HCMVMIE) promoter (SEQ ID NO: 1, GenBank: K03104.1, full length 930b) (FIG. 3, p42CMV, SEQ ID NO: 2). As the HGF, an HGF in which a native human HGF gene sequence was replaced with a human frequent codon (codon optimized human HGF; optHGF, SEQ ID NO: 4) was used. In FIG. 2, a region underlined with a single line indicates a mutated ITR region (SEQ ID NO: 12), a region underlined with a double line indicates a non-mutated ITR region (SEQ ID NO: 13), and a region underlined with a thick line indicates simian virus 40 (SV40) poly A signal (SEQ ID NO: 15). The mutated ITR has a mutation configured to allow a vector genome produced from pVector-p42 to self-complement and is shorter than a wild type ITR. The non-mutated ITR is also shorter than the wild type ITR.

The obtained vector plasmid (pVector-p42) was transfected into host cells (HEK293EB). Specifically, $2.0\times10^6$ HEK293EBs were seeded on Corning® 245 mm Square BioAssay Dish (Corning), cultured for 2 days, and then transfected using Polyethylene MAX (40,000 MW, linear; Polysciences, Inc.; hereinafter PEI). The compositions are as shown in Table 1 (amount per one square dish). pAAV2RC-3M is a plasmid containing Rep gene and Cap gene of AAV2, and has a mutation in which three tyrosines in a capsid protein VP3 are replaced with phenylalanine (Y444, 500, 730F).

TABLE 1

| Solution A | | Solution B | | DMEM(−) + GlutaMax | |
|---|---|---|---|---|---|
| pHelper | 44.8 μg | PEI (2 μg/mL) | 135 μL | DMEM (−) | 40 mL |
| pVector-p42 | 44.8 μg | DMEM (−) | 5.3 mL | 100 × GlutaMax | 0.5 mL |
| pAAV2RC-3M | 44.8 μg | | | | |
| DMEM (−) | 5.3 mL | | | | |

PEI: Polyethylene MAX
GlutaMax: GlutaMax-I (100×) (Life Technologies Corporation )

The culture medium was replaced with DMEM/2% FBS/GlutaMax 6 to 12 hours after transfection. The cells were further cultured for 3 days and then were collected with PBS. The culture medium was adjusted to 5 mL per dish.

The cells in PBS were vortexed with a vortex mixer, and then were disrupted by repeating freeze-thawing 5 times using liquid nitrogen and a thermostat bath at 37° C. 10 U/mL Benzonase (25 U/mL, Novagen) containing 5 mM $MgCl_2$ was added to the suspension after the disruption. The suspension was reacted at 37° C. for 30 minutes. The reaction was stopped by the addition of EDTA (final concentration 5 mM). The reacted solution was centrifuged at 12,000 rpm (R12A2) for 30 minutes at 4° C., and only the supernatant was collected. The collected supernatant was heated at 50° C. for 30 minutes and further centrifuged twice at 10,000 rpm for 10 minutes at 4° C. to collect the supernatant. The collected supernatant was filtered through a 0.45 μm-pore filter (Millex-HV, Millipore) equipped with a prefilter (Millex-AP, Millipore).

An equal amount of saturated ammonium sulfate solution was added to the filtrate. The filtrate was mixed by inversion, and then incubated in ice water for 30 minutes. The precipitate was collected as a pellet by centrifugation at 12,000 rpm for 30 minutes at 4° C. 32 mL of ice-cold PBS per a pellet amount of 10 to 20 square dishes was added to the pellet, and the pellet was resuspended, and then placed in an Ultra-Clear centrifuge tube (25×89 mm, Beckman). 3 mL of 1.25 g/mL $CsCl_2$ in HNE buffer (refractive index (RI)=1.361) was added to a bottom of the tube. 3 mL of 1.74 g/mL $CsCl_2$ in HNE buffer (RI=1.402) was further added to the bottom of the tube without breaking the layer. The tube was ultracentrifuged at 30,000 rpm for 2.5 hours at 16° C. (Optima L-70K Ultracentrifuge, Beckman Coulter; Sw 32 Ti rotor) (Accel, Deccel; Max). After the centrifugation, a Beckman Fraction Recovery System (#270331580, Beckman) was used to collect only a solution of the layer having 1.368 to 1.376 of RI. The collected solution was immediately dialyzed in 500 mL of PBS/3 mM $MgCl_2$ buffer using Slide-A-Lyzer G2 Dialysis Cassette (Thermo Fisher, 20KMWCO, 3 mL capacity). After the dialysis under stirring with a stirrer for 2 hours or more, the buffer was exchanged. The buffer exchange was performed 4 times. The solution containing the virus after the dialysis was collected in 1.5 mL Eppendorf tube, and centrifuged (Centrifuge 5417R, Eppendorf) at 10,000 rpm for 5 minutes at 4° C. The supernatant containing scAAV2TM.mCMV.optHGF was collected.

Based on the same method, an ssAAV2TM.p13CMV.optHGF.WPRE (AAV.p13), which is a single-strand rAAV2, was also prepared. The vector plasmid (pVector-p13) has a nucleotide sequence of SEQ ID NO: 6. A CMV promoter (p13CMV, SEQ ID NO: 3) as a promoter was used. An optHGF (SEQ ID NO: 4) as an HGF was used. As shown in FIG. 3, p13CMV is longer than p42CMV. WPRE-mut6 (WPRE; Woodchuck Hepatitis Virus Post-transcriptional Regulatory Element, SEQ ID NO: 7) was placed between the optHGF and the ITR located at the 3' end side in pVector-p13. The two ITRs of pVector-p13 are both non-mutated.

Example 2

Intravitreal Administration in Mice

Examination with NMDA Model

Animals

In this example, 8-week-old male C57BL/6 mice (CLEA Japan, Inc.) were used. The mice were bred with free access to food and drinking water under light/dark cycle for 14-hour/10-hour.

Intravitreal Administration

The mice were anesthetized by intraperitoneal administration of ketamine/xylazine (100 mg/kg, 10 mg/kg) and eye drops of oxybuprocaine hydrochloride (Benoxir ophthalmic solution 0.4%, Santen Pharmaceutical Co., Ltd.). 1 μL of the viral vector (AAV.p42) was intravitreally administered to each of the anesthetized mice. 1 μL of N-methyl-D-aspartic acid (NMDA, Wako) was intravitreally administered to each of the mice three weeks after the virus administration. The concentrations of the virus and NMDA are shown in Table 2.

TABLE 2

| Virus | Genome titer (v.g./mL) | Viral dose (v.g.) | NMDA concentration (nmols/μL) |
|---|---|---|---|
| AAV.p42 | 1.0 × 10E+13 | 1.0 × 10E+10 | 5 |

In Vivo hHGF RNA Expression Level Analysis

Real-time PCR was performed to analyze expression level of hHGF RNA in retina of each of the mice. The mice were euthanized by cervical dislocation under isoflurane anesthesia four weeks after the virus administration. Eyeballs were removed from the mice. Each of neural retinas (layer consisting of inner limiting membrane, nerve fiber layer, ganglion cell layer, inner plexiform layer, inner granular layer, outer plexiform layer, outer granular layer, outer limiting membrane and photoreceptor layer) was peeled off under an ophthalmic microscope. Each of the obtained membranes (hereinafter, neural retina) was immersed in 200 μL of RNAlater (Qiagen) overnight at 4° C. and then stored at −30° C. Each of the neural retinas was transferred to 350 μL of Buffer RLT/β-mercaptoethanol (100:1), and each of the neural retinas was disrupted by sonication. RNA extraction from each of the neural retinas was performed using RNeasy Minikit (Qiagen) according to a product manual.

The obtained RNA was converted to cDNA by reverse transcription PCR using TaKaRa RNA PCR™ Kit ((AMV) Ver.3.0, TaKaRa) according to the conditions shown in Table 3.

TABLE 3

| Solution | | Temperature conditions | |
|---|---|---|---|
| 25 mM $MgCl_2$ | 4 μL | Step 1: 30° C. | 10 min |
| 10 × RT Buffer | 2 μL | Step 2: 42° C. | 20 min |
| dNTPs | 2 μL | Step 3: 95° C. | 5 min |
| RNase inhibitor | 0.5 μL | Step 4: 4° C. | ∞ |
| RTranscriptaseXL | 1 μL | | |
| Random 9mers primer | 1 μL | Step 4 is a waiting step at the end | |
| RNA + milliQ $H_2O$ | 9.5 μL | | |
| (RNA; 145 ng) | Total 20 μL | | |

Using the obtained cDNA as a template, real-time PCR was performed using SYBR (registered trademark) Premix Ex Taq™ (Tli RNaseH Plus) (Takara) according to the conditions shown in Table 4. The sequences of primers are listed in Table 5.

TABLE 4

| Solution | | ΔΔ Ct | |
|---|---|---|---|
| SYBR Premix | 10 μL | Step 1: 95° C. 10 sec | |
| ROX Reference DyeII | 0.4 μL | Step 2: 95° C. 5 sec | |
| 10 μM F primer | 0.4 μL | | 40 times |
| 10 μM R primer | 0.4 μL | Step 3: 60° C. 34 sec | |
| milliQ $H_2O$ | 6.8 μL | Step 4: 95° C. 15 sec | |
| +templates | 2 μL | Step 5: 60° C. 1 min | |
| Total | 20 μL | Step 6: 95° C. 30 sec | |
| | | Step 7: 60° C. 15 sec | |

TABLE 5

| | |
|---|---|
| Forward primer (optHGF) | TACCGGAACAAGCACATCTG (SEQ ID NO: 8) |
| Reverse primer (optHGF) | TTCATCAGCACCAGGTCG (SEQ ID NO: 9) |
| Forward primer (GAPDH) | CATCACTGCCACCCAGAAGA (SEQ ID NO: 10) |
| Reverse primer (GAPDH) | ATGTTCTGGGCAGCC (SEQ ID NO: 11) |

Results

In Vivo hHGF RNA Expression Level Analysis

Figure 4:
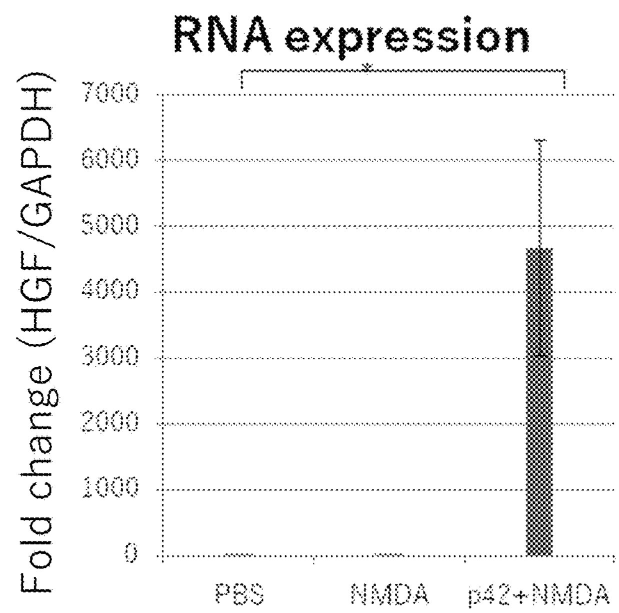
FIG. 4 shows a graph depicting the expression of hHGF RNA in AAV.P42 administration group (p42+NMDA group) or AAV.P42 non-administration groups (PBS group and NMDA group).

The results are shown in FIG. 4. In the AAV.p42-administered group (p42+NMDA group), 4746±1634-fold (±S.E.) hHGF RNA expression was observed as compared to the AAV.p42-untreated group (PBS group) (mean±S.E., t-test, *p<0.05, n=3 (n=2 for NMDA group)).

Example 3

In Vivo Protein Expression Analysis

Each of the neural retinas obtained in Example 2 was immersed in PBS and then cooled on ice. The neural retinas were crushed by sonication to obtain samples containing the crushed neural retinas HGF protein expression level in each of the neural retinas was analyzed using the Human HGF Quantikine ELISA Kit (R&D) according to the product manual. Absorbance of the solution in each well was measured at 450 nm by a plate reader (ARVO MX Perkin Elmer 1420 Multilabel Counter).

Total protein amount of each of the neural retinas was measured using the total protein assay by DC protein assay kit. 5 μL of standard and each sample (standard: 1.0, 0.5, 0.25, 0.125, 0 mg/mL (PBS), sample: 4-fold diluted sample with PBS) were placed in each well of a 96 well plate and 25 μL of Reagent A was added to each well. After adding 200 μL of Reagent B to each well, the 96 well plate was shaken for 5 seconds and incubated at room temperature for 15 minutes. Absorbance of the solution in each well was measured by a plate reader (ARVO MX Perkin Elmer 1420 Multilabel Counter) at 750 nm.

Result

In Vivo Protein Expression Analysis

Figure 5:
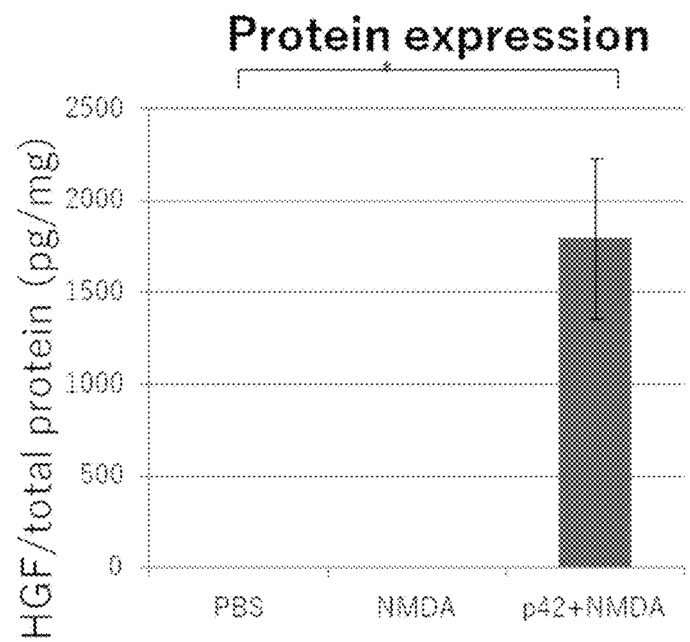
FIG. 5 shows a graph depicting the expression of hHGF protein in AAV.P42 administration group (p42+NMDA group) or AAV.P42 non-administration groups (PBS group and NMDA group).

The results are shown in FIG. 5. An amount of hHGF protein per total protein amount in each neural retina in the AAV.p42 administration group (p42+NMDA group) was 1796±439 pg/mg (±S.E.) (mean±S.E., t-test, $*p<0.05$, n=3 (NMDA group: n=2)), which was different from the amounts of the protein in the AAV.p42 non-administered groups (PBS group and NMDA group). The viral vector AAV.p42 was administered into a vitreous of each normal tension glaucoma model mouse. As a result, suppression of decrease in the number of cells in each ganglion cell layer was observed (not shown).

Example 4

In Vitro Protein Expression Analysis

The HGF expression levels in mouse neuroblastoma cell line Neuro2a and mouse striated muscle cell line C2C12 were analyzed. $1\times10^5$ (cells/well) of each cell was seeded and cultured on a 24-well plate. $5\times10^5$ v.g. of the AAV.p42 per one cell was added to the C2C12 wells in 6 hours after the seeding, and $5\times10^5$ v.g. of the AAV.p42 per one cell was added to the Neuro2a wells in 20 hours after the seeding. After culturing for 1 day, the cells in each well were washed with 500 μL of PBS, and then 500 μL of DMEM/10% FBS was added to each well. The cells were cultured for 2 days and the supernatants were collected. The collected supernatants were centrifuged at 3000 rpm for 5 minutes at 4° C., and the supernatant samples were used for the analysis. According to the same method, the AAV.p13 was transduced into C2C12 and Neuro2a, and supernatant samples were obtained from each.

The HGF expression level analysis was performed according to the method described in Example 3. The supernatant samples were diluted to 20 times with RDSP buffer of Human HGF Quantikine ELISA Kit and then used.

Figure 6A:
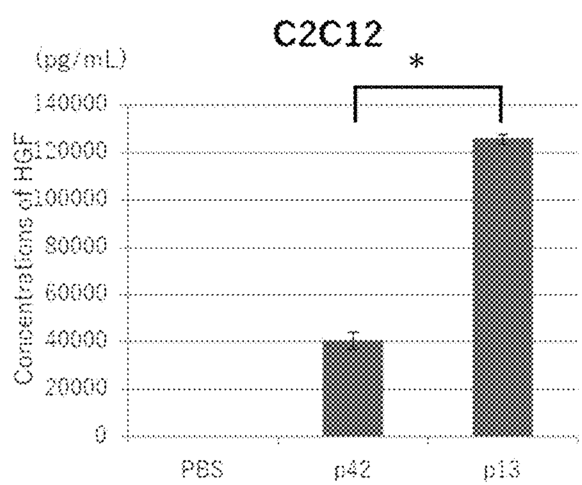
FIG. 6A shows a graph depicting hHGF secretion in C2C12 cells infected with AAV.P42 or AAV.P13.
Figure 6B:
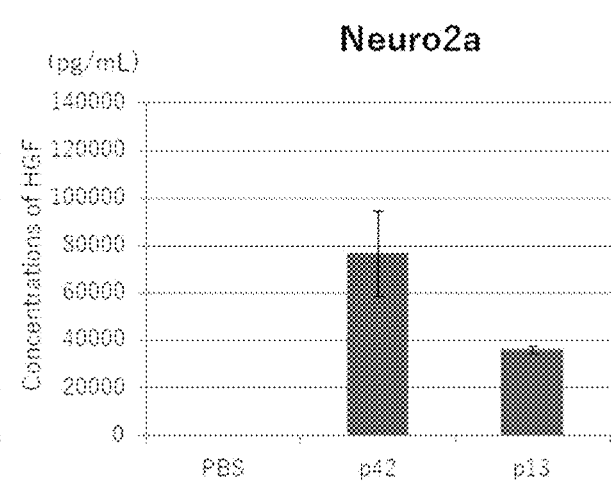
FIG. 6B shows a graph depicting hHGF secretion in Neuro2a cells infected with AAV.P42 or AAV.P13.

The results are shown in FIGS. 6A and B. Remarkable hHGF secretions were observed in both C2C12 cells and Neuro2a cells (mean±S.E., t-test, $*p<0.05$, n=3). Particularly, higher level expression was observed in Neuro2a cells as compared with the single chain AAV.p13 having the same HGF sequence. From the above results, it was revealed that truncation of the wild type CMV promoter region did not significantly affect the expression of hHGF.

Summary

The present inventors have decided to use the self-complementary adeno-associated virus (scAAV) vector because the gene expression efficiency is low in the above-mentioned general ssAAV vector. Since the scAAV vector is a double-stranded DNA from the beginning, the expression efficiency of the carried gene is high, while the length of the gene that can be carried is halved compared to the ssAAV. Therefore, it has been considered that HGF having a total length of about 2.2 kbp can be carried in the general ssAAV, but it is difficult to carry it in the scAAV. The present inventors removed the unknown sequence on the AAV vector through earnest study. Furthermore, we succeeded in carrying the HGF into the scAAV vector by deleting part of the promoter region of the CMV and part of the ITR region of the AAV.

It was experimentally observed that the scAAV vector according to the present invention can express the HGF at a high level in vitro and in vivo as compared with the conventional AAV vector. Specifically, when the amounts of HGF proteins in the culture supernatants of the mouse neuroblastoma cell line (Neuro2a) and mouse myoblast cell line (C2C12) transduced with the vector were measured by the ELISA method, high levels of HGF protein secretions were observed in both cell lines. In particular, it was observed that the HGF protein in Neuro2a infected with the vector was more remarkably expressed than that in Neuro2a infected with single-chain AAV having the same HGF sequence as the vector. When the mRNA expression level and protein expression level of HGF in the in which acute retinal damage was induced by N-methyl-D-aspartic acid after a certain expression period of the vector administered into the mouse vitreous were measured by real-time PCR and ELISA, it was observed that the HGF was highly expressed in the damaged retina. In addition, when the vector was administered to a normal-tension glaucoma model mouse, a decrease in the number of cells on the ganglion cell layer was suppressed (not shown).

The pVector-p42 (SEQ ID NO: 5) used in the above examples is created based on an empty vector (pVector; SEQ ID NO: 16). Although the pVector-p42 was carried with HGF, the pVector can be carried with factors other than HGF (for example, neurotrophic factors, growth factors and cytokines). In addition, the pVector can be carried with a promoter other than CMVIE.

We claim:

1. A vector plasmid for producing a vector genome to be carried in an adeno-associated virus (AAV) vector, comprising a vector genome cassette as a template of the vector genome, wherein the vector plasmid comprises:

(1) an expression cassette comprising (a) a target gene-encoding nucleic acid molecule, and (b) an expression control region-encoding nucleic acid molecule capable of controlling expression of the target gene; and (2) two inverted terminal repeat (ITR)-encoding nucleic acid molecules located so as to sandwich the expression cassette, the two ITR-encoding nucleic acid molecules comprise a non-mutated ITR-encoding nucleic acid molecule and a mutated ITR-encoding nucleic acid molecule, the mutated ITR-encoding nucleic acid molecule has a mutation configured such that a vector genome capable of self-complementation is obtained from the vector genome cassette, the length of the non-mutated ITR-encoding nucleic acid molecule and the length of the mutated ITR-encoding nucleic acid molecule are shorter than the length of the native ITR-encoding nucleic acid molecule thereof, and the target gene is a hepatocyte growth factor (HGF) gene.

2. The vector plasmid according to claim 1, wherein the mutated ITR-encoding nucleic acid molecule is located upstream from the non-mutated ITR-encoding nucleic acid molecule in a 5'-end direction.

3. The vector plasmid according to claim 1, wherein the vector genome comprises the expression cassette, a reverse complementary expression cassette comprising a nucleic acid molecule encoding a reverse complementary sequence of the expression cassette, and the mutated ITR-encoding nucleic acid molecule located between the expression cassette and the reverse complementary expression cassette.

4. The vector plasmid according to claim 1, wherein the mutated ITR-encoding nucleic acid molecule comprises a nucleotide sequence of SEQ ID NO: 12.

5. The vector plasmid according to claim 1, wherein the non-mutated ITR-encoding nucleic acid molecule comprises a nucleotide sequence of SEQ ID NO: 13.

6. The vector plasmid according to claim 1, wherein the expression control region is a truncated expression control region, and a length of the truncated expression control region is shorter than a length of a native expression control region thereof.

7. The vector plasmid according to claim 6, wherein the truncated expression control region has a function as a promoter.

8. The vector plasmid according to claim 6, wherein the native expression control region is a cytomegalovirus expression control region.

9. The vector plasmid according to claim 8, wherein the cytomegalovirus expression control region has a cytomegalovirus major immediate early promoter region.

10. The vector plasmid according to claim 9, wherein the cytomegalovirus expression control region has a nucleotide sequence of SEQ ID NO: 1.

11. The vector plasmid according to claim 6, wherein the truncated expression control region is SEQ ID NO:2 or SEQ ID NO:3.

12. The vector plasmid according to claim 1, wherein the HGF gene is a human HGF gene.

13. The vector plasmid according to claim 12, wherein a codon in the human HGF gene is replaced with a human frequent codon.

14. The vector plasmid according to claim 12, wherein the human HGF gene has a nucleotide sequence of SEQ ID NO:4.

15. An AAV vector carrying the vector genome produced from the vector plasmid according to claim 1.

16. The AAV vector according to claim 15, for treating or preventing an eye disease or a disease associated therewith.

17. A pharmaceutical composition for treating or preventing an eye disease or a disease associated therewith, comprising the AAV vector according to claim 15.

* * * * *